United States Patent
Ortner et al.

(10) Patent No.: US 8,473,019 B2
(45) Date of Patent: Jun. 25, 2013

(54) PATIENT INTERFACE FOR SPECTROSCOPY APPLICATIONS

(75) Inventors: Joseph P. Ortner, Hutchinson, MN (US); Bryan J. Scheele, Hutchinson, MN (US)

(73) Assignee: Hutchinson Technology Incorporated, Hutchinson, MN (US)

( * ) Notice: Subject to any disclaimer, the term of this patent is extended or adjusted under 35 U.S.C. 154(b) by 1006 days.

(21) Appl. No.: 12/507,934

(22) Filed: Jul. 23, 2009

(65) Prior Publication Data

US 2009/0287071 A1   Nov. 19, 2009

Related U.S. Application Data

(62) Division of application No. 11/129,935, filed on May 16, 2005, now Pat. No. 7,596,397.

(51) Int. Cl.
*A61B 5/1455* (2006.01)

(52) U.S. Cl.
USPC .......................... 600/322; 600/323; 600/344

(58) Field of Classification Search
USPC ................. 600/310, 322, 323, 324, 340, 473, 600/476; 602/58
See application file for complete search history.

(56) References Cited

U.S. PATENT DOCUMENTS

| | | |
|---|---|---|
| 3,972,329 A | 8/1976 | Kaufman |
| 4,223,680 A | 9/1980 | Jobsis |
| 4,537,197 A | 8/1985 | Hulka |
| 4,653,498 A | 3/1987 | New, Jr. et al. |
| 4,817,623 A | 4/1989 | Stoddart et al. |
| 4,825,879 A | 5/1989 | Tan et al. |
| 4,830,014 A | 5/1989 | Goodman et al. |
| 4,865,038 A | 9/1989 | Rich et al. |
| 4,932,684 A | 6/1990 | Vermeulen |
| 4,964,408 A | 10/1990 | Hink et al. |
| 5,094,240 A | 3/1992 | Muz |
| 5,111,817 A | 5/1992 | Clark et al. |
| 5,222,495 A | 6/1993 | Clarke et al. |
| 5,224,478 A | 7/1993 | Sakai et al. |
| 5,237,994 A | 8/1993 | Goldberger |

(Continued)

FOREIGN PATENT DOCUMENTS

| | | |
|---|---|---|
| EP | 0 127 947 | 12/1984 |
| EP | 0 568 380 | 11/1993 |

(Continued)

OTHER PUBLICATIONS

Bruce A. Crookes, et al., "Can Near-Infrared Spectroscopy Identify the Severity of Shock in Trauma Patients?", The Journal of Trauma Injury, Infection, and Critical Care, vol. 58, No. 4, Apr. 2005, pp. 806-816, XP009073413.

(Continued)

*Primary Examiner* — Eric Winakur
(74) *Attorney, Agent, or Firm* — Faegre Baker Daniels LLP

(57) ABSTRACT

A patient interface and method of locating the patient interface for use particularly in spectroscopy applications. The patient interface includes a concave region and first and second convex regions. A wing extends from the concave region to help locate the patient interface properly. The convex regions provide additional adhesion support, particularly when used on the thenar eminence. The patient interface may be placed in a number of locations on a patient to determine an optimum location for measurement prior to affixing the interface to the patient.

21 Claims, 26 Drawing Sheets

U.S. PATENT DOCUMENTS

| | | | |
|---|---|---|---|
| 5,267,563 A | 12/1993 | Swedlow et al. | |
| 5,392,783 A | 2/1995 | Fogarty et al. | |
| 5,402,777 A | 4/1995 | Warring et al. | |
| 5,411,023 A | 5/1995 | Morris et al. | |
| 5,584,296 A | 12/1996 | Cui et al. | |
| 5,642,733 A | 7/1997 | Archibald et al. | |
| 5,680,857 A * | 10/1997 | Pelikan et al. | 600/323 |
| 5,842,982 A | 12/1998 | Mannheimer | |
| 5,879,373 A | 3/1999 | Roper et al. | |
| 6,061,584 A | 5/2000 | Lovejoy et al. | |
| 6,091,975 A | 7/2000 | Daddona et al. | |
| 6,095,974 A | 8/2000 | Shemwell et al. | |
| 6,101,405 A | 8/2000 | Yasuda et al. | |
| 6,377,829 B1 | 4/2002 | Al-Ali | |
| 6,381,489 B1 | 4/2002 | Ashibe | |
| 6,415,167 B1 | 7/2002 | Blank et al. | |
| 6,428,515 B1 * | 8/2002 | Bierman et al. | 604/174 |
| 6,473,632 B1 | 10/2002 | Myers | |
| 6,487,343 B1 | 11/2002 | Lewandowski et al. | |
| 6,527,711 B1 | 3/2003 | Stivoric et al. | |
| 6,556,851 B1 | 4/2003 | Ott et al. | |
| 6,671,532 B1 * | 12/2003 | Fudge et al. | 600/344 |
| 6,725,075 B2 | 4/2004 | Al-Ali | |
| 6,839,579 B1 | 1/2005 | Chin | |
| 6,839,583 B1 | 1/2005 | Lewandowski et al. | |
| 2002/0038080 A1 | 3/2002 | Makarewicz et al. | |
| 2002/0165440 A1 | 11/2002 | Mason et al. | |
| 2003/0069484 A1 | 4/2003 | Blank et al. | |
| 2003/0166998 A1 | 9/2003 | Lowery et al. | |
| 2003/0181799 A1 | 9/2003 | Lindekugel et al. | |
| 2004/0147822 A1 | 7/2004 | Al-Ali et al. | |
| 2004/0167382 A1 | 8/2004 | Gardner et al. | |
| 2005/0054908 A1 | 3/2005 | Blank et al. | |

FOREIGN PATENT DOCUMENTS

| | | |
|---|---|---|
| EP | 0 587 009 | 3/1994 |
| EP | 0 816 829 | 1/1998 |
| JP | 2004 351107 | 12/2004 |
| WO | WO 97/01985 | 1/1997 |
| WO | WO0178587 A2 | 10/2001 |
| WO | WO 02/28274 | 4/2002 |
| WO | WO 03/024303 | 3/2003 |
| WO | WO 2005/027720 | 3/2005 |

OTHER PUBLICATIONS

Bruce A. McKinley, et al., "Tissue Hemoglobin O2 Saturation during Resuscitation of Traumatic Shock Monitored Using Near Infrared Spectrometry", The Journal of Trauma Injury, Infection, and Critical Care, vol. 48, No. 4, Apr. 2000, pp. 637-642, XP009073412.

Partial European Search Report issued in EP 10 01 0021, date of completion Nov. 9, 2010, 3 pages.

European Search Report issued in EP 10010019, completed Nov. 12, 2010, 9 pages.

* cited by examiner

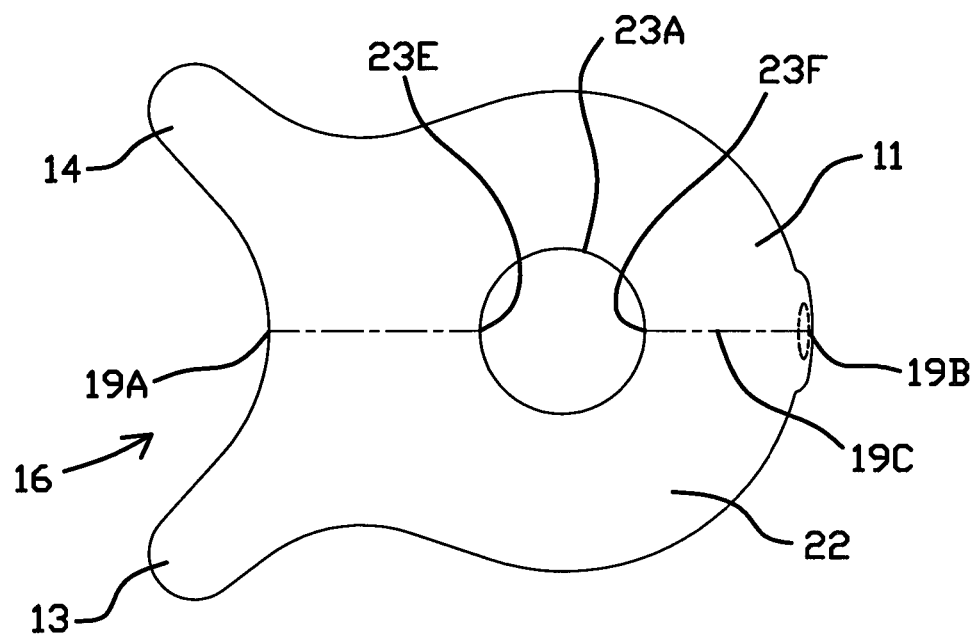
FIG. 1G
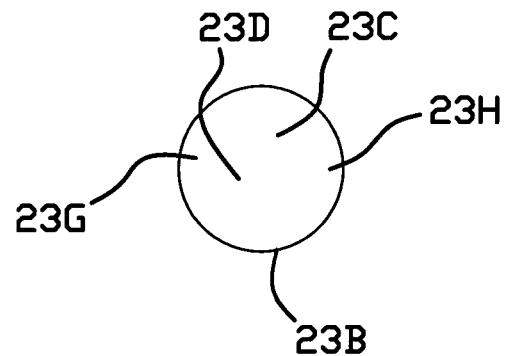

PATIENT INTERFACE FOR SPECTROSCOPY APPLICATIONS

CROSS-REFERENCE TO RELATED APPLICATION

This application is a divisional of application Ser. No. 11/129,935, filed May 16, 2005, entitled "PATIENT INTERFACE FOR SPECTROSCOPY APPLICATIONS," which is herein incorporated by reference in its entirety.

The present invention relates to the field of medical spectroscopy and more specifically to the field of mounting sensors on a patient for use in spectroscopy.

The use of spectroscopy in medical condition diagnosis has become commonplace. Typically, light is placed on the surface of tissue in one location and transmitted or scattered light is collected from the tissue in another location. A spectral analysis of the collected light is then performed and the results are compared to stored information about spectral profiles of tissue having known conditions. From this comparison, the condition of the tissue under study may be determined.

The light to be transmitted into the tissue is typically placed on the tissue through use of an optical head. The same optical head may be used to collect the light. Some spectroscopy systems allow for collection of light that passes through tissue and therefore one optical head is used for light transmission while a second optical head is used for collection.

The optical head may be held directly on the tissue by a doctor, nurse or technician, it may be directly taped or strapped into place, an external structure may hold it in place or it may be held securely in place through a patient interface. A patient interface is a specially designed structure that will typically hold the optical head within its structure and includes an adhesive, suction, compressive, strapping, or other (e.g. glove like) structures to hold the patient interface securely to the patient's tissue. Some examples of patient interfaces are shown in U.S. Pat. Nos. 4,223,680, 4,537,197, 4,653,498 (the "New" patent), U.S. Pat. Nos. 4,817,623, 4,825,879 (the "Tan" patent), U.S. Pat. No. 4,830,014 (the "Goodman" patent), U.S. Pat. No. 4,865,038 (the "Rich" patent), U.S. Pat. No. 4,964,408 (the "Hink" patent), U.S. Pat. Nos. 5,094,240, 5,111,817 (the "Clark" patent), U.S. Pat. Nos. 5,224,478, 5,267,563, 5,402,777, 5,584,296, 5,879,373 and 6,381,489.

It has been found that performing blood spectroscopy on the fingers allows for access to a significant quantity of blood vessels that are near the surface of the skin. Accordingly, a number of patents have been directed to such patient interfaces mountable on a finger, such as the New, Tan, Goodman, Rich, Hink and Clark patents.

A problem with spectroscopy of fingers is that the patient interfaces or the attachment straps tend to wrap entirely around the finger. Blood flow to the finger can be thereby restricted and this can affect the accuracy of the spectroscopy.

Further, some locations on the body present more blood vessels near the surface than others. Even within a short range of a location that provides a reasonable level of blood vessels for measurement, a better location may exist. However, the prior art suffers from an inability to relocate the sensor easily once the sensor has been affixed to the tissue.

SUMMARY OF THE INVENTION

The present invention is a device and process for assisting in locating a fixture for measurement of an attribute of tissue, such as the percentage of oxygenated hemoglobin present in the tissue. In one embodiment, a fixture for holding a light source and a light path to a sensor or the sensor itself includes a base approximately shaped to a thenar muscle of a hand, the base including a passage for light transmission and collection therethrough. A first wing portion is connected to the base. The first wing portion may be partially wrapped around a body part when the fixture is in use. A second wing portion connected to the base whereby the second wing portion may be partially wrapped around the body part in an opposite direction from the first wing may also be included. The fixture may also include a concave region formed between the two wings for providing a locating feature for the fixture.

In another embodiment, a patient interface for a tissue measurement instrument, includes an elongated, flexible base member having a first rounded end and a second rounded end. The base member has a passage for light transmission therethrough. A first wing extends from the second end for partially wrapping around a body part to which the interface will be attached. The patient interface may include first and second ends that are convex rounded ends. The patient interface may further include a second wing extending from the second end and first and second convex regions extending from the first end. Alternatively, the first end of the patient interface may have a convex rounded end while the second end is a concave rounded end. In still another alternative, the patient interface has a second wing extending from the second end.

In yet still another alternative embodiment, the base member includes first and second holes allowing for light transmission therethrough. A light source is provided for providing light to pass through the first hole while a light path (such as an optical fiber) is aligned with the second hole for collecting light that has passed through tissue and adapted to transmit a signal representative of the collected light.

In still another embodiment, the patient interface has a longitudinal axis between the first rounded end and the second rounded end and the first and second holes lie substantially on the longitudinal axis.

The patient interface has a top and bottom side. In an embodiment, the bottom side is adapted to be placed in contact with the patient, and an adhesive is located on the bottom side while a first liner is used to cover the adhesive. In a variant to this embodiment, a second liner may be used in conjunction with the first liner. The first liner then covers a first portion of the adhesive while the second liner covers another portion of the adhesive.

In yet another embodiment of the patient interface, a structure for aiding in the measurement of an attribute of tissue includes a base having a concave locating feature and a longitudinal axis that substantially bisects the locating feature and send and receive fibers each having ends, the ends lying in a line generally along the longitudinal axis and being substantially coplanar when in use.

Another embodiment includes a base having a concave locating feature and a longitudinal axis that substantially bisects the locating feature and send and receive light ports generally along the longitudinal axis, the send and receive light ports being substantially coplanar when in use.

One more embodiment contains a base having a concave locating feature and a longitudinal axis that substantially bisects the locating feature and an elongated opening lying generally along the longitudinal axis, the elongated opening lying generally in a plane when in use.

The invention also is a method of locating a patient interface for a tissue measurement instrument on a patient. Typically, the patient interface has a measurement side with a light transmission hole and a light receipt hole. The process includes the steps of moving the patient interface around on the tissue in a particular region of the body until a desired threshold reading is achieved on the tissue measurement instrument. Then, upon finding the location where a desired threshold reading is achieved, temporarily placing the patient interface to the patient for a predetermined amount of time and finally affixing the patient interface to the patient. The process may also include the steps of generally aligning the light transmission hole and the light receipt hole along one of a adductor pollicus, a thenar eminence, a hypo thenar eminence, a digit, a first dorsal interosseous or a deltoid muscle.

In another process for attaching the patient interface to a patient, for locating a tissue measurement instrument on a patient the process includes moving the patient interface around on the tissue in a particular region of the body until a location where a desired threshold reading is achieved on the tissue measurement instrument is found. Then, upon finding the location where a desired threshold reading is achieved, the patient interface is firmly held to the patient. Then, the patient interface is partially removed from the patient while holding it in place so that a first amount of adhesive on the measurement side of the patient interface may be readied for attachment to the patient. Next, the first amount of exposed adhesive is placed on the patient. Then, the patient interface is partially removed in a second direction so that a second amount of adhesive may be readied for attachment to the patient. Finally, the second amount of exposed adhesive is placed on the patient. In additional steps to this process, the first amount of adhesive is activated by removing one of the first and second liners; and the second amount of adhesive is activated by removing the other of the first and second liners.

In still another embodiment, a method of locating a patient interface for a tissue measurement instrument is described. The patient interface includes an elongated, flexible base member having a first rounded end, the base member having a passage for light transmission therethrough and at least first and second wings extending from the first end each for partially wrapping around a body part to which the interface will be attached wherein the first end is a concave end. The method of placement includes locating the concave end generally transverse the shoulder axially aligned with the deltoid. The patient interface is then affixed to the patient.

In further steps to this process, the patient interface can include an adhesive on a patient facing surface and a split liner can be used to cover the adhesive until the patient interface is to be affixed to the patient. The process then includes the further steps of lifting a first portion of the patient interface from the patient; removing a first piece of the split liner, placing the first portion of the patient interface back on the patient, lifting a second portion of the patient interface from the patient, removing a second piece of the split liner, and placing the second portion of the patient interface back on the patient.

There is yet one more process for locating the patient interface on a patient, where the patient interface has a generally concave locating edge and a measurement side with a light transmission hole and a light receiving holed aligned generally along an axis bisecting the concave locating edge. The process includes the steps of locating the concave locating edge proximate the base of a digit and aligning the light transmission hole and the light receiving hole along a major muscle group to be measured.

Yet another structure for aiding in the measurement of an attribute of tissue includes a base having a patient side and an adhesive on the patient side, the adhesive having at least first and second adhesive regions. A split liner having first and second portions covers the first and second adhesive regions respectively. The first portion has a first adhesive facing region attached to the adhesive, a first hinge region, a first patient facing region connected to the first adhesive facing region through the first hinge region and a first tab extending beyond the base. The second portion has a second adhesive facing region attached to the adhesive, a second hinge region, a second patient facing region connected to the second adhesive facing region through the second hinge region and a second tab extending beyond the base. A method of placing such a patient interface includes the steps of placing a base on a patient. The base has a patient side and an adhesive on the patient side. The adhesive has at least first and second adhesive regions. A split liner having first and second portions covers the first and second adhesive regions respectively. The first portion has a first adhesive facing region attached to the adhesive, a first hinge region, a first patient facing region connected to the first adhesive facing region through the first hinge region and a first tab extending beyond the base. The second portion has a second adhesive facing region attached to the adhesive, a second hinge region, a second patient facing region connected to the second adhesive facing region through the second hinge region and a second tab extending beyond the base. The first and second portions meet to form a separation. A user pulls on the first tab in a direction substantially normal to the separation and pulls on the second tab in a direction substantially normal to the separation.

BRIEF DESCRIPTION OF THE DRAWING

FIG. 1G is a bottom view of an alternative embodiment of the patient interface with a single round hole.

DETAILED DESCRIPTION OF THE PREFERRED EMBODIMENT

Figure 1:
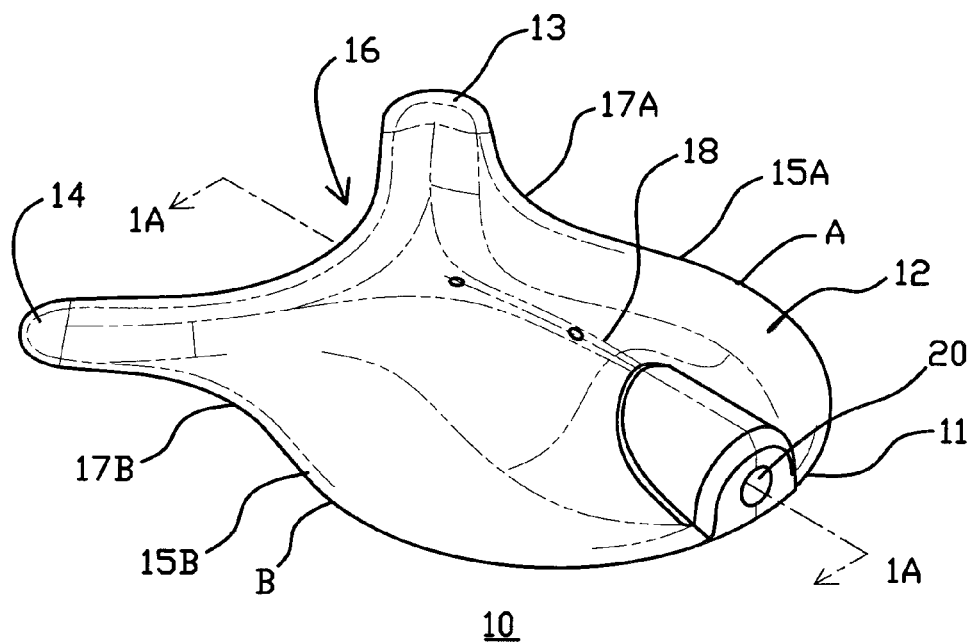
FIG. 1 is a perspective view of a patient interface of the present invention.

Referring now to FIG. 1, thereshown is a patient interface 10 for use with a tissue spectrometer (not shown). The patient interface includes base 12, wings 13 and 14, convex regions 15A and B, concave region 16, pocket 18 and opening 20. The base 12 may have a semi-circular portion between points A and B and extend in convex regions 15A and B. The convex regions are intended to engage peripheral portions of the thenar eminence or other sites when positioned for use on the hand. The convex regions are also intended to shield ambient light while engaging the peripheral portions of the thenar eminence. The convex regions 15A and B lead into concave regions 17A and B which are intended to roughly follow the narrowing of the thenar eminence or other sites at its distal end. Wings 13 and 14 are for partially wrapping around the thumb or other sites of the patient. Concave region 16 serves as a locating feature such as at the base of the thumb or other finger or a pediatric shoulder for example. Other locating features such as v shapes or notches are also contemplated. Concave region 16, located between the wings, is intended to engage the patient's thumb approximately at the intersection of the first metacarpal bone (or the other metacarpal bones) with the hand.

Figure 10:
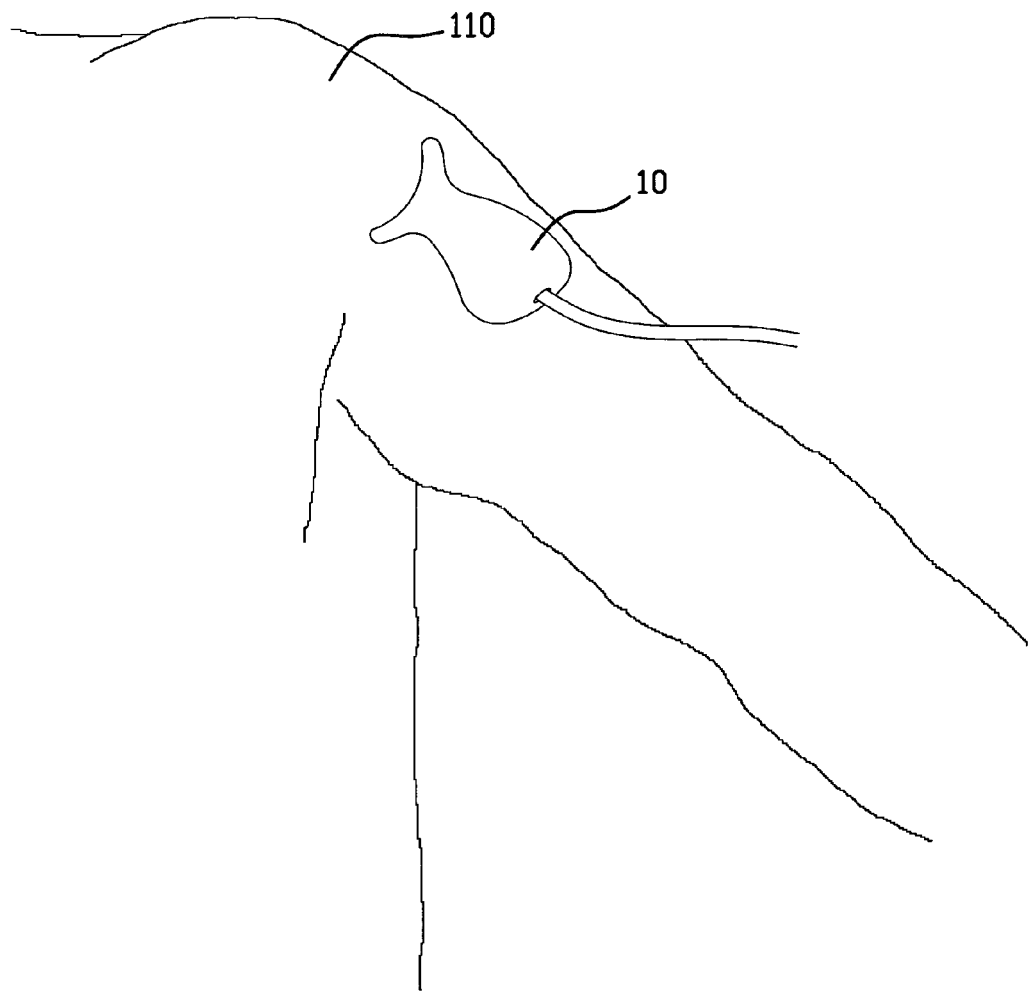
FIG. 10 is an elevation view of a patient interface on a patient's deltoid muscle.

Alternatively, the present patient interface can be used for spectroscopy applications on baby or small child in the deltoid region of the child's arm as shown in FIG. 10.

Figure 1A:
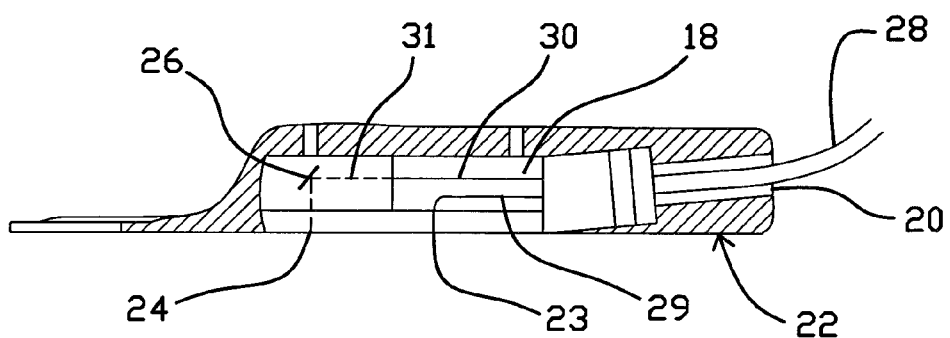
FIG. 1A is a slice view taken along line 1A-1A of the patient interface shown in FIG. 1.
Figure 1B:
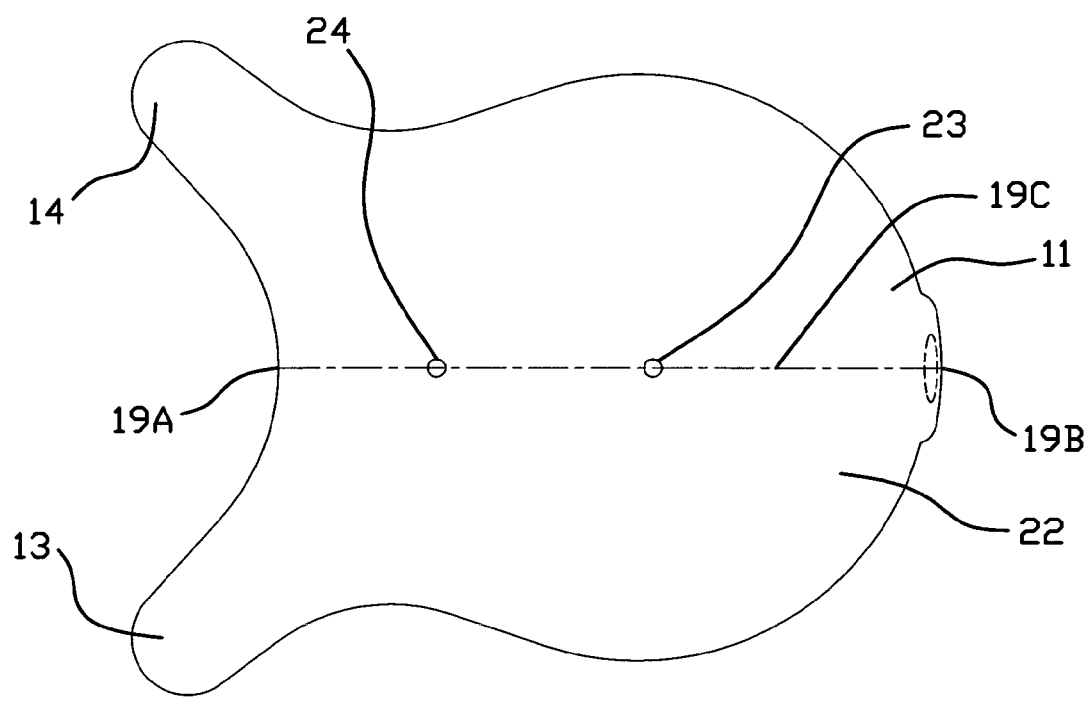
FIG. 1B is a bottom view of the patient interface in FIG. 1.

The bottom of the patient interface (FIG. 1B) shows an essentially flat patient surface 22 with holes 23 and 24 therein. Hole 24 is preferably for light transmission into the patient while hole 23 is for collecting light from the patient into a return transmission to the spectrometer. The holes, particularly hole for receiving light is preferably located near the center of the convex region so that additional shielding from ambient light is provided. As can be seen in the slice view FIG. 1A, opening 20 provides a path for fiber optic cable 28 to reach the inside of pocket 18. There, a light transmission fiber 30 is provided with a path to transmit light to the patient. Here, fiber 30 terminates and light exits the fiber and is reflected through hole 24 by mirror 26. Light returning from tissue (not shown) is collected through hole 23 into light return fiber 29 for transmission to the spectrometer for analysis. In one embodiment, the holes 23 and 24 are at least approximately co-axial with an axis 19C extending between a centerpoint 19A of the concave region 16 and a centerpoint 19B of first end 11. In another embodiment, a mirror is positioned inside the opening to reflect light onto a receive fiber. It should be noted that while one preferred embodiment has been described, there are many other possible methods of transmitting light to tissue and collecting and transmitting the return light signal back to the spectrometer.

In an alternative embodiment, a single elongated hole 23A is used to replace holes 23 and 24. In such an embodiment, an integrated sensor head may be used to hold light transmission and light receiving paths in place and to isolate the light receiving path from the light transmission path. The single elongated hole has the elongation generally aligned with axis 19C.

Figure 1C:
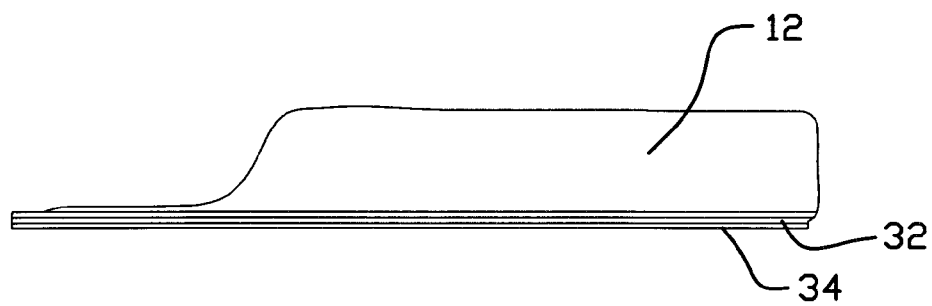
FIG. 1C is a side view of the patient interface of FIG. 1 further including an adhesive layer and a release liner layer.

Referring now to FIG. 1C, thereshown is a side view of the patient interface 10 with adhesive 32 and liner 34. In operation it is desirable for the patient interface to adhere to the patient. Adhesive 34 may be an entire layer, a pattern (such as dots of adhesive), lines of adhesive or virtually any other method of distributing adhesive on the patient surface 22. The adhesive itself is generally chosen so that it is compatible with human tissue and does not create a permanent bond. One adhesive that may be used is 3M 1524 adhesive. Other adhesives having hypoallergenic properties would also be acceptable. Alternatively, belts, tape, Velcro® fasteners and gloves as well as other well known attachment methods may be used. The liner 34 covers the adhesive until the patient interface is ready for affixing. It is made of a material that will lightly adhere to the adhesive, but is easy to remove at the point that the patient interface is ready to be used.

Figure 1D:
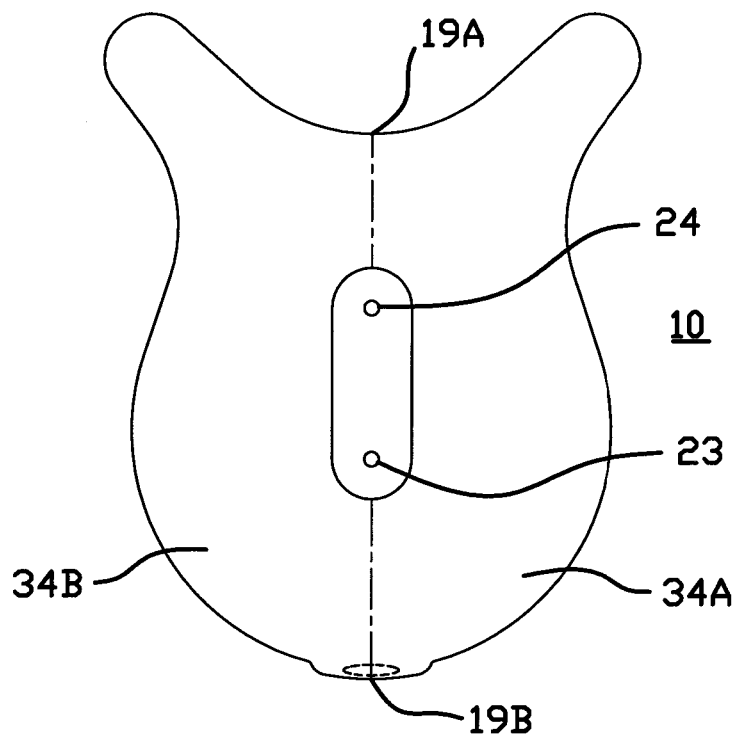
FIG. 1D is a bottom view of the patient interface of FIG. 1 with a split liner.
Figure 1E:
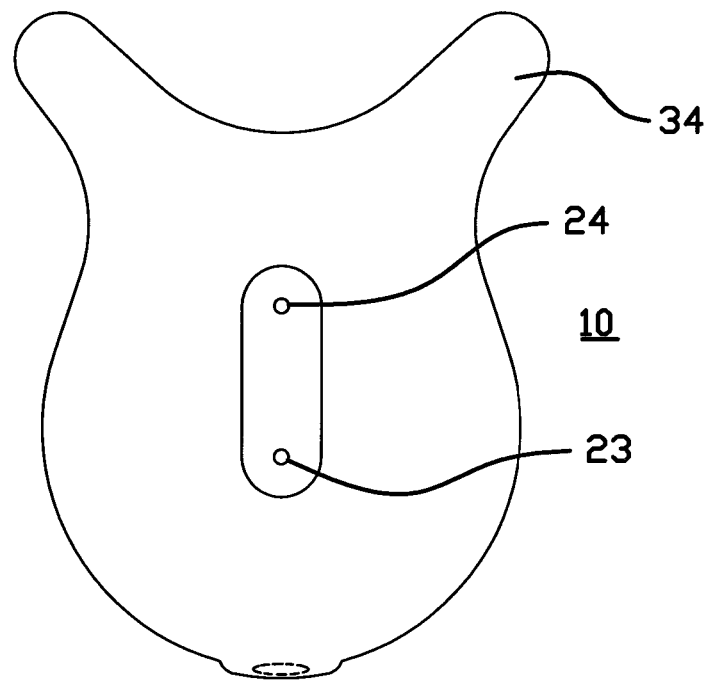
FIG. 1E is a bottom view of the patient interface with a single piece liner.
Figure 1F:
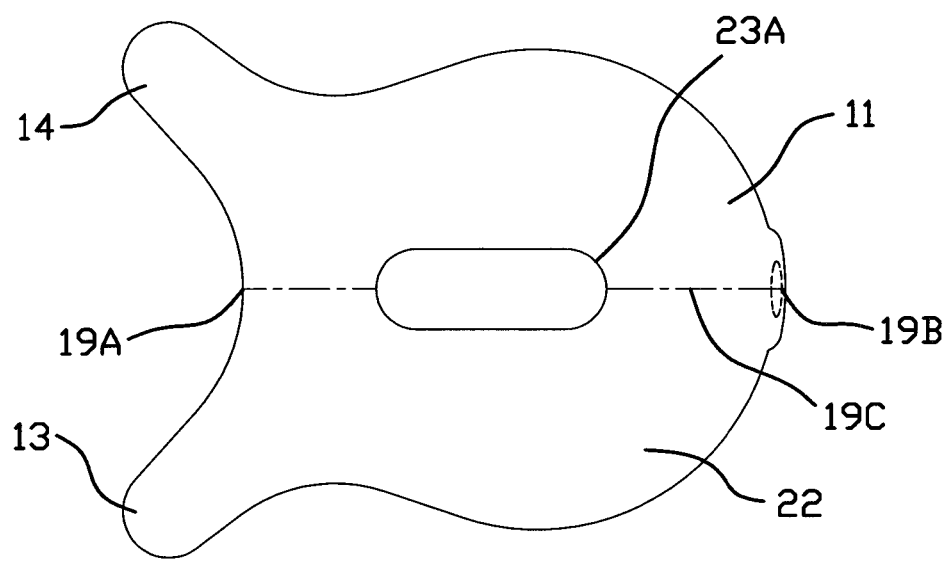
FIG. 1F is a bottom view of an alternative embodiment of the patient interface with a single elongated hole.

As can be seen in FIG. 1D, the liner 34 may be split into two pieces 34A and 34B. This allows for the liner to be removed in two steps without lifting the interface completely off the patient. Other arrangements where something other than an even split between the liner pieces may be used as well. In FIG. 1E, the liner is shown as a single piece 34 that covers the entire patient side of the interface.

Figure 2A:
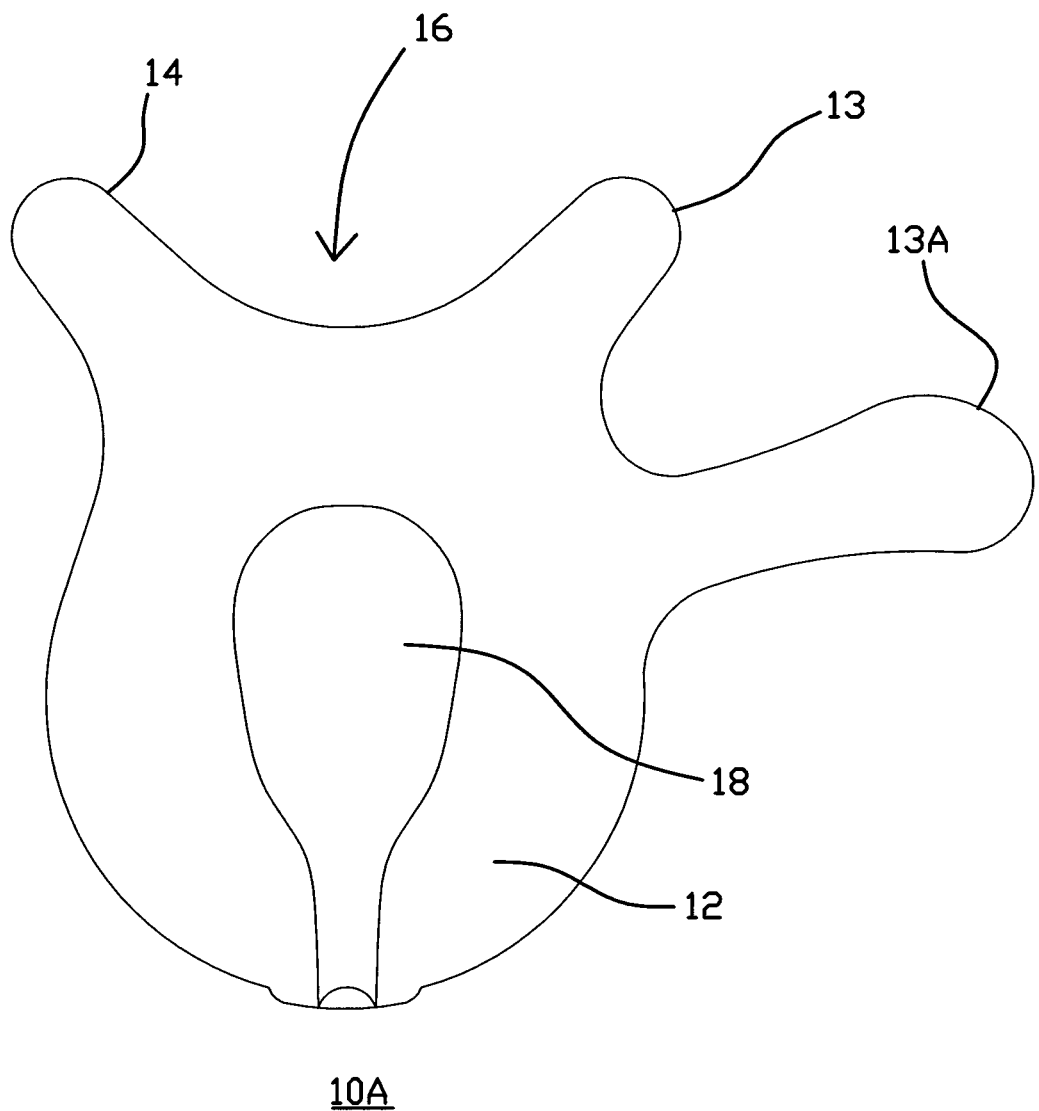
FIG. 2A is a top view of a second embodiment of the patient interface.
Figure 2B:
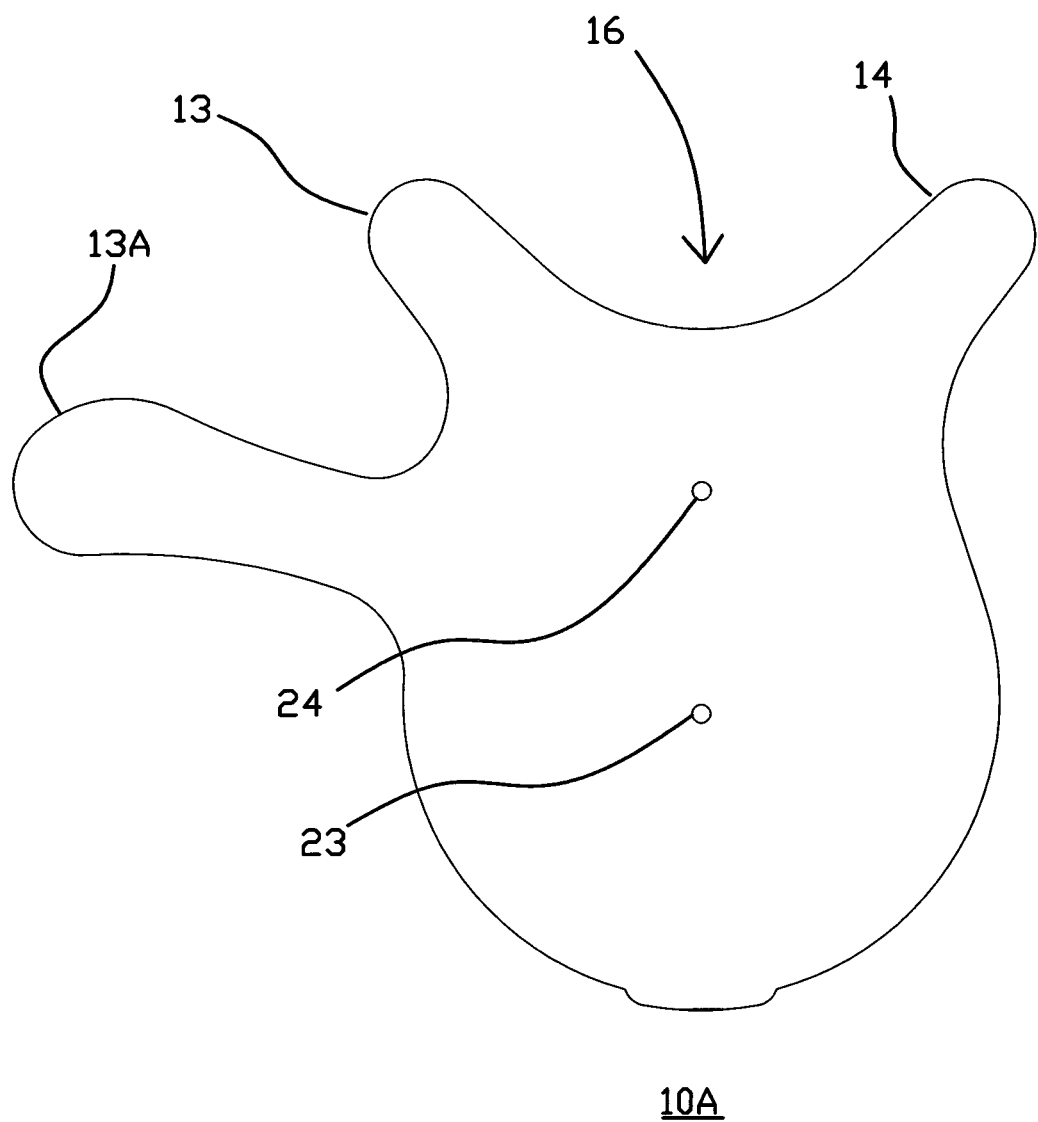
FIG. 2B is a bottom view of the second embodiment of the patient interface.

Referring now to FIGS. 2A-B thereshown are top and bottom views of a second embodiment of the patient interface 10A. This patient interface is essentially the same as the patient interface of FIG. 1 except that it includes an additional wing 13A. The reason for the additional wing will become apparent in connection with the discussion of FIGS. 5A-D.

The patient interface may be made of a soft polymer material such as Santoprene available from Exxon Mobile Chemicals. Rubber, foam and other soft, pliable materials may also be used. The interfaces may be formed by through injection molding. Alternatively, the patient interface may be formed in an upper and lower piece and ultrasonically welded together.

Figure 4A:
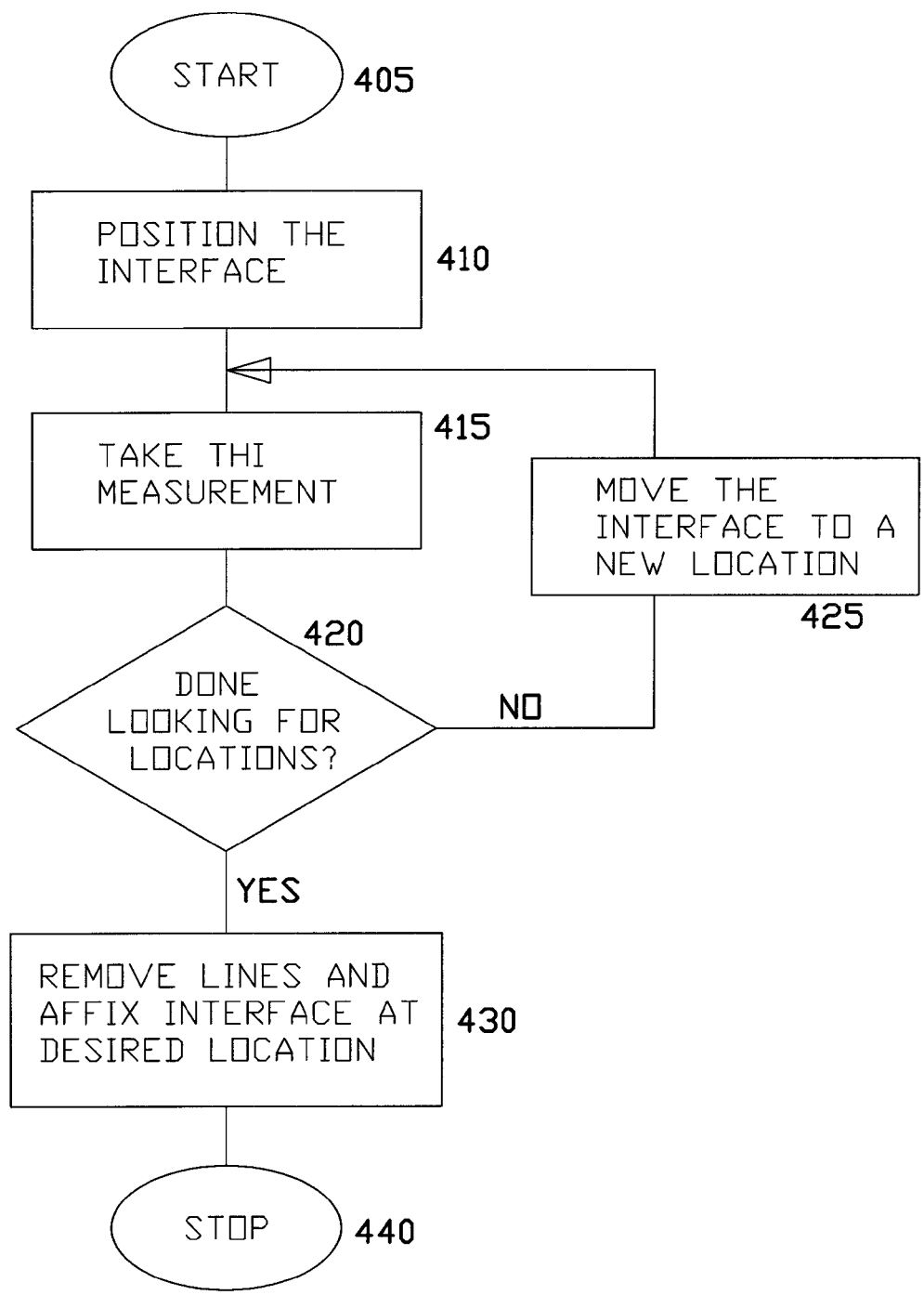
FIGS. 4A-B are a flow charts of two processes for placing the patient interface.

Switching now to the method of placement of the patient interface, a flowchart of two such methods is shown in FIGS. 4A and B. Referring now to FIG. 4A, it is desirable to locate the patient interface at a location having a predetermined THI measurement. This will provide a suitable location from which to measure hemoglobin oxygenation. In one case, a local maximum THI value is sought and the patient interface is moved while the output of the spectrometer is monitored. The user then locates the interface in a position providing a highest reading. In an alternative process, a threshold level of THI is sought by moving the interface. Once the threshold has been found, the interface is attached to the patient. In one embodiment, the threshold is a two percent tissue hematocrit value.

The process for locating the interface using THI measurements includes starting at block 405, and moving to block 410 where a patient interface, connected to a tissue spectrometer, is put into a first position. Then at block 415, a THI measurement is taken. In block 420, the user determines whether any further locations need to be tested. Such a determination may be made using the above noted minimum threshold THI method or the maximum THI method.

If more THI values are needed, then, the patient interface is moved to a new position in block 425 and a new THI measurement is taken again in block 415. If a new measurement is not needed, then the patient interface can be held in place while the liner is removed and the patient interface is adhered to the patient as specified in block 430. The process would then end at block 440.

Alternatively, a higher localized temperature may also be sensed to provide an indication of the amount of blood flow through a portion of tissue in place of a THI value. In this instance, a temperature sensor would be mounted in the interface and the interface would be moved until a local maximum temperature is found and then the interface would be attached at the location of the local maximum temperature. Other sensors that may indicate a local maximum of blood flow may be used. The key is that it is preferable to place the interface where a local maximum of blood flow may occur and that the sensing method used for placement provide some indication of local blood flow.

Figure 4B:
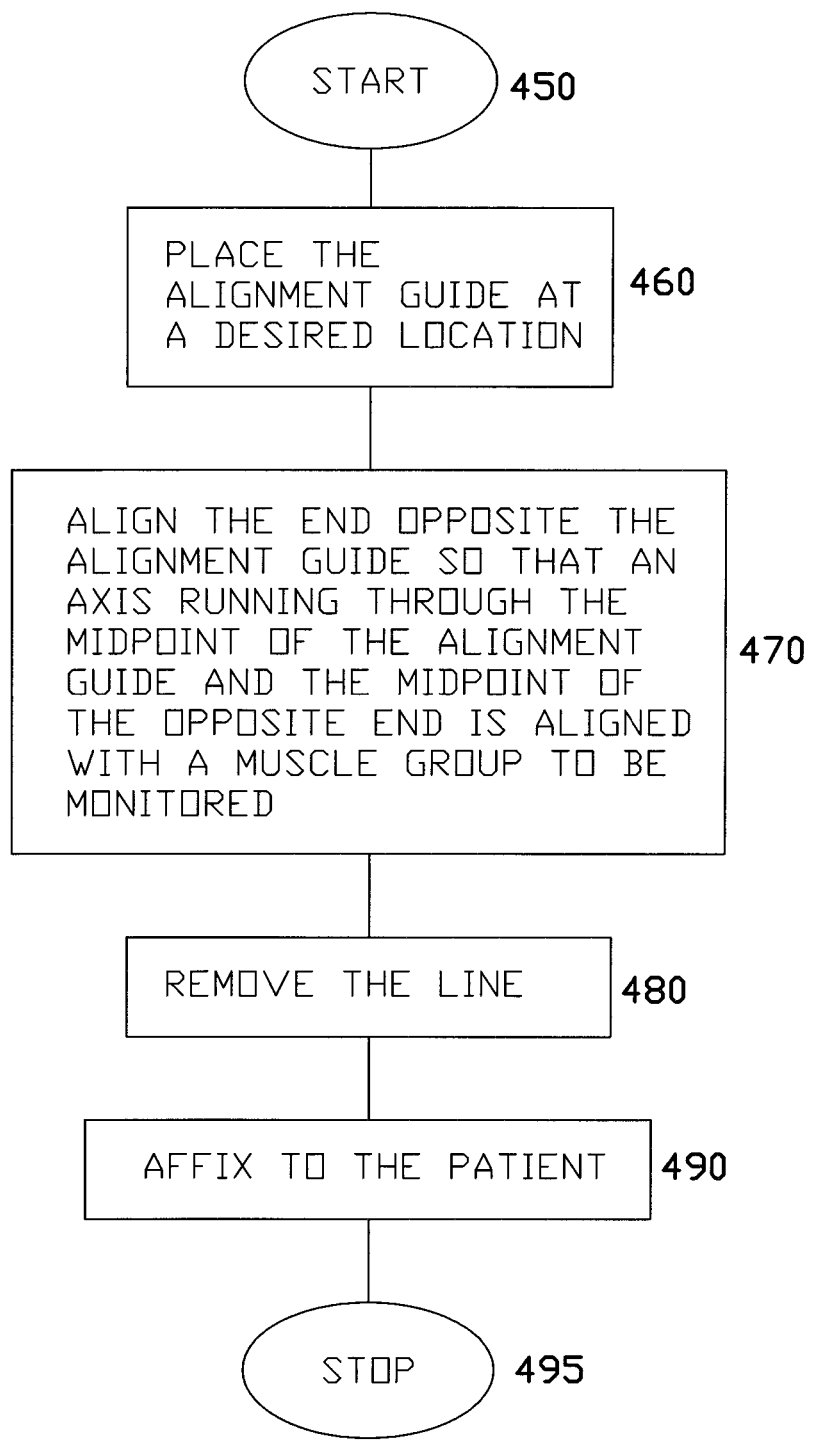

Alternatively, the locating feature of the patient interface may be used without a blood flow measurement to aid in placement the patient interface as shown in FIG. 4B. After starting at block 450, the process moves to block 460 where the alignment guide of the patient interface is placed in a desired location (such as the base of a finger). Next, the opposite end of the patient interface is located so that an axis running through the midpoint of the patient locating feature and the opposite end is aligned with a muscle to be monitored as described in block 470. The liner is then removed as in block 480 and the interface is affixed to the patient in 490 before the process ends in block 495.

There are at least three ways of removing the liner as described in block 430. First, a single liner may be used. Once the location having the desired THI value is located, the patient interface may be tilted to one side at the desired location and the single liner removed. The patient interface may then be placed back onto the patient. In the case where a split liner is used, the patient interface may be placed at the location having the desired THI value and the patient interface is partially lifted so that one side of the split liner may be removed. The patient interface is then replaced on the patient so that the adhesive that has been uncovered attaches to the patient. The other side of the patient interface may then be lifted and the liner removed and the lifted portion is again replaced on the patient. Lastly, a "butterfly" liner may be used (as described herein) for removal of the liner without lifting of the patient interface.

THI may be calculated using the process specified in U.S. Pat. No. 6,473,632 ("Myers") commonly assigned with the present patent. By using the combination of both a single term ratio of a second derivative light absorbance value of tissue and a single term non-ratioed second derivative light absorbance value of the tissue, measure of the volume percentage of a chromophore such as hemoglobin in tissue (a value that directly correlates with hemoglobin concentration) can be calculated (the above noted THI).

In one configuration the wavelength gap used to calculate the second derivative values (i.e., the interval between adjacent absorbance wavelengths used in the second derivative calculation) is 40 nm. At this gap size only four wavelengths are used to calculate both the percentage of oxidized hemoglobin and the THI. The second derivative absorbance peak at 720 nm (deoxyhemoglobin absorption band of 760 nm) is used to empirically derive the relationship between THI and second derivative absorbance. Second derivative gap sizes other than 40 nm can also be used to derive the hematocrit algorithm. Also, other wavelength regions (e.g., visible or infrared) corresponding to other oxyhemoglobin or deoxyhemoglobin absorbance maximums could be used.

The THI measurements made in accordance with the algorithms described herein can be used by an instrument in connection with tissue recognition algorithms. Inaccurate and/or invalid measurements of % StO2 or other measured parameters can be displayed by the instrument monitor if the probe is not properly located on the tissue to be measured. The THI can be used by the instrument to determine whether the probe is properly positioned and the measurement is accurate. For example, in connection with some or all of the parameter measurements, the instrument can compute the THI using the algorithm described herein, and display the parameter measurement as an accurate measurement only if the THI is representative of a predetermined minimum level. If the THI is below the predetermined level, the monitor can generate a display indicating that the probe is not properly positioned.

THI measurements can be generated as a function of current second derivative spectroscopy values and stored data describing the relationship between the second derivative values and the tissue hemoglobin concentration. In the embodiment described below, the stored relationship data is data describing a set of lines or slopes (or curves if preferred), each of which is associated with a constant oxidation state of hemoglobin.

During THI, the proper stored relationship data can be selected by the instrument on the basis of the measured hemoglobin oxidation state. From this data and the current second derivative spectroscopy value, the THI can be computed by the instrument.

At multiple levels of hematocrit (HCT), the second derivative spectral features of the blood are recorded at a predetermined (e.g., 5 mm) probe spacing over multiple % StO2 values within the 0%-100% range. For each hematocrit the 720 nm second derivative peak is fitted to a linear equation.

At each constant level of % StO2, the second derivative 720 nm feature is related to % hematocrit with extrapolation to 0% hematocrit. There is a linear relationship between the 720 nm second derivative and hematocrit at hematocrits of about 25% and less.

Using linear extrapolation to 0% hematocrit and empirical measurements at 25% and 15% hematocrit, a lookup table of relationship data which describes the sensitivity of hematocrit to the 720 nm second derivative values (lines of constant % StO2) can be created. The slopes are functionally related to the ratio of the second derivative at 680 nm to the second derivative at 720 nm.

The stored relationship data described above is subsequently used during tissue hemoglobin concentration measurements. Upon measuring % StO2 (e.g., using conventional algorithms and scaled second derivative values at 680 nm) the corresponding slope value (Mso2 or HCT slope) is found within the lookup table. The predicted hematocrit value is then:

$$\% HCT = (Mso2) \times (D720/PSF)$$

Where: D720 is the second derivative at 720 nm using the 40 nm gap PSF is the relative path length change due to probe spacing.

The concentration of tissue hematocrit is generally less than 25%, and is usually in the 1%-10% range. When evaluating probe position on the basis of hemoglobin concentration measurements, relatively high measurement accuracy near the lower end of the range is sufficient. For example, the threshold for determining whether the probe is on or off tissue can be in the range of 1% measured hemoglobin concentration. The linear range of spectral features versus hematocrit concentration need only be used for this application. However, in accordance with the present invention, the measurement accuracy can be extended to greater percentages of hematocrit by redefining the algorithm to account for nonlinearities. The algorithm could, for example, be redefined as a multiple regression algorithm consisting of multiple slope and second derivative transformations (linear transformations). Examples of nonlinear equations include:

$$\% HCT = (Mso2_1) \times (D720/PSF) + (Mso2_2) \times \text{Log}(D720/PSF)$$

or $$\% HCT = (Mso2_1) \times (D720/PSF) + (Mso2_2) \times (D720/PSF)^{1/2} + (Mso2_3) \times (D720/PSF)^{1/3} + \ldots$$

Where: $Mso2_1$, $Mso2_2$, ... are nonlinear slope value coefficients which can be stored in the lookup table.

The probe scaling factor (PSF) can be empirically determined by collecting second derivative spectral measurements of a chromophore medium, preferably having constant scattering and absorption properties, with optical probes having variable distances between the optical send and receive fibers.

The spectral measurements at each probe spacing are then referenced (ratioed) to one of the fixed probe spacing spectral measurements at a particular wavelength of interest. The ratio of one second derivative spectrum value at a probe spacing of interest to the second derivative spectrum value of the reference probe spacing then reflects the probe scaling factor. The probe scaling factor can be determined at calibration stored in memory.

Figure 3A:
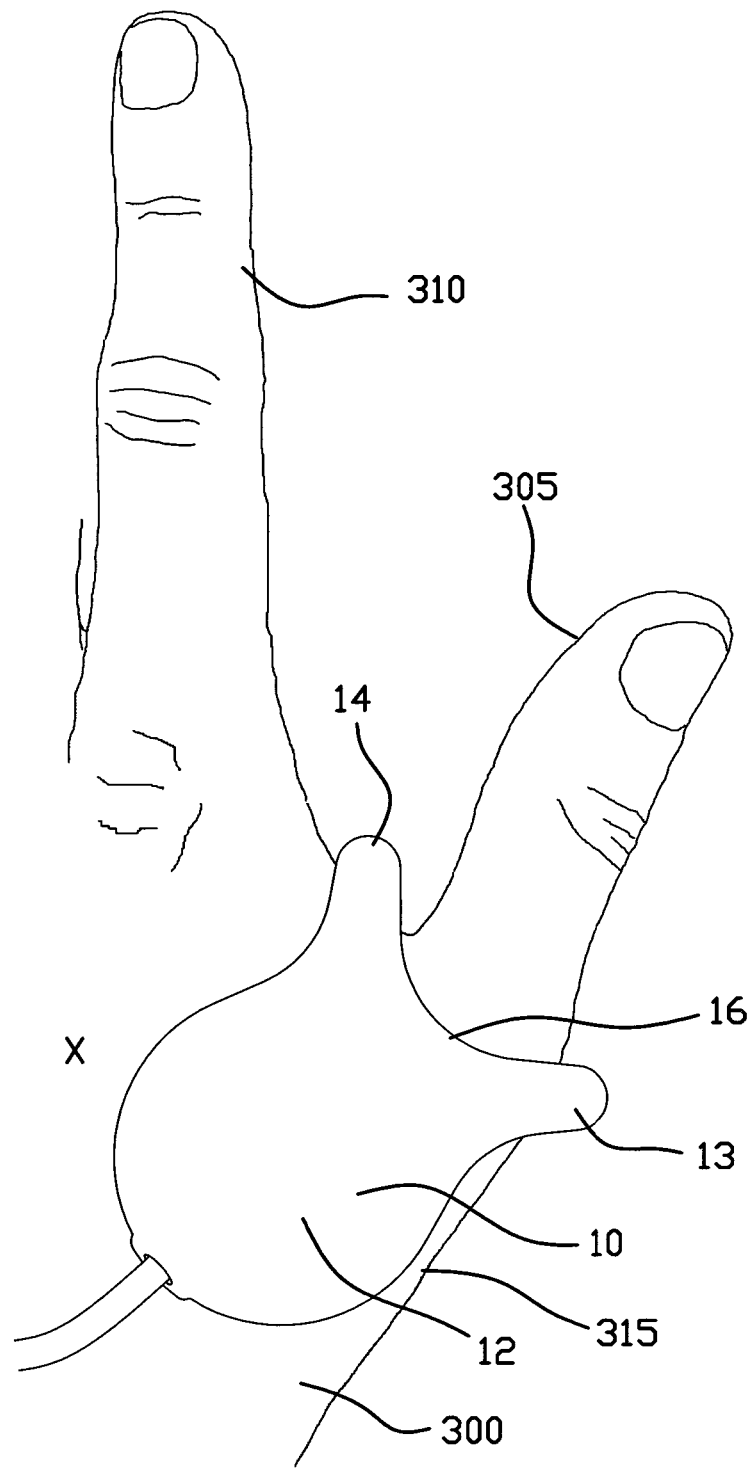
FIGS. 3A-C are perspective views of a patient interface being placed on a hand.
Figure 3B:
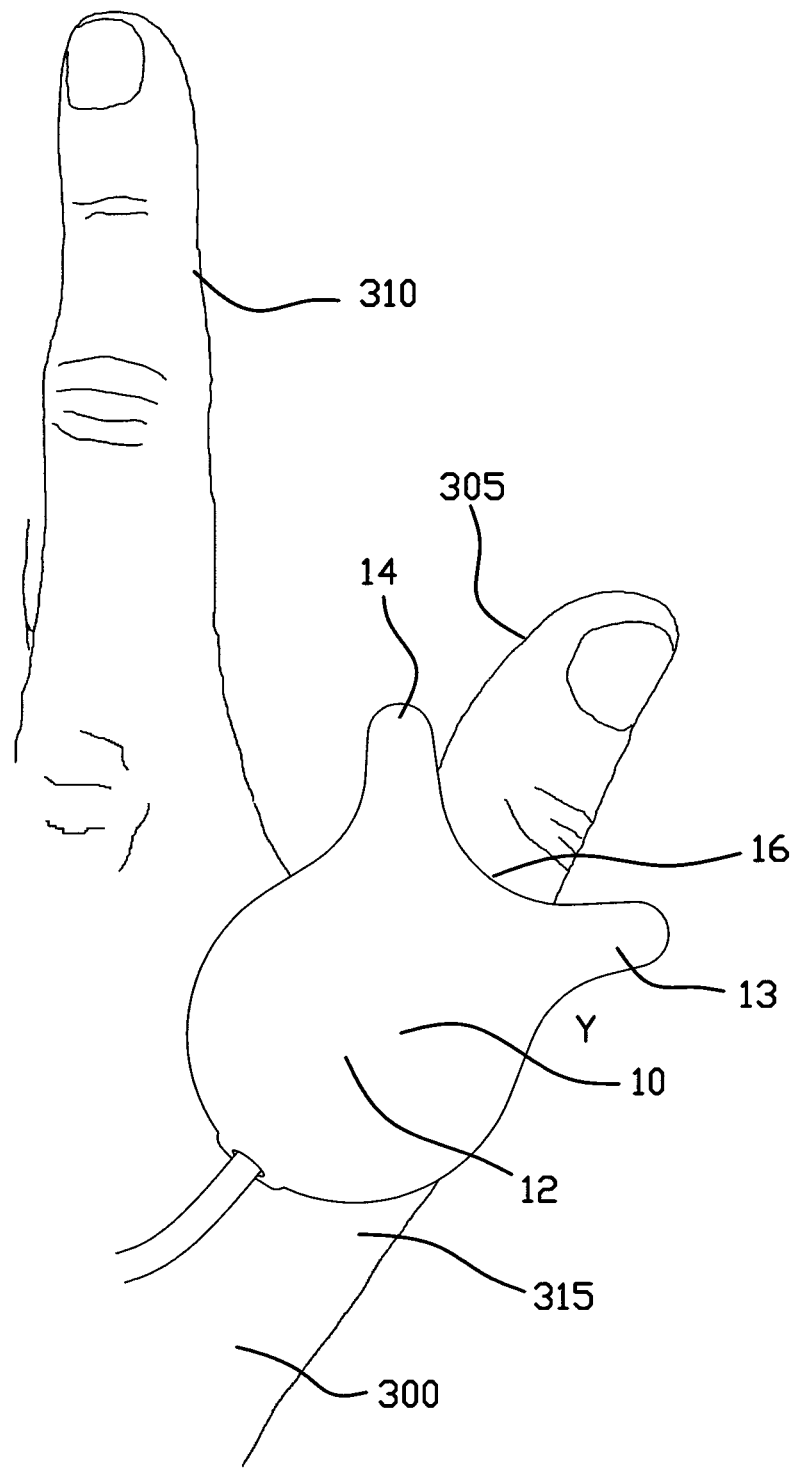
Figure 3C:
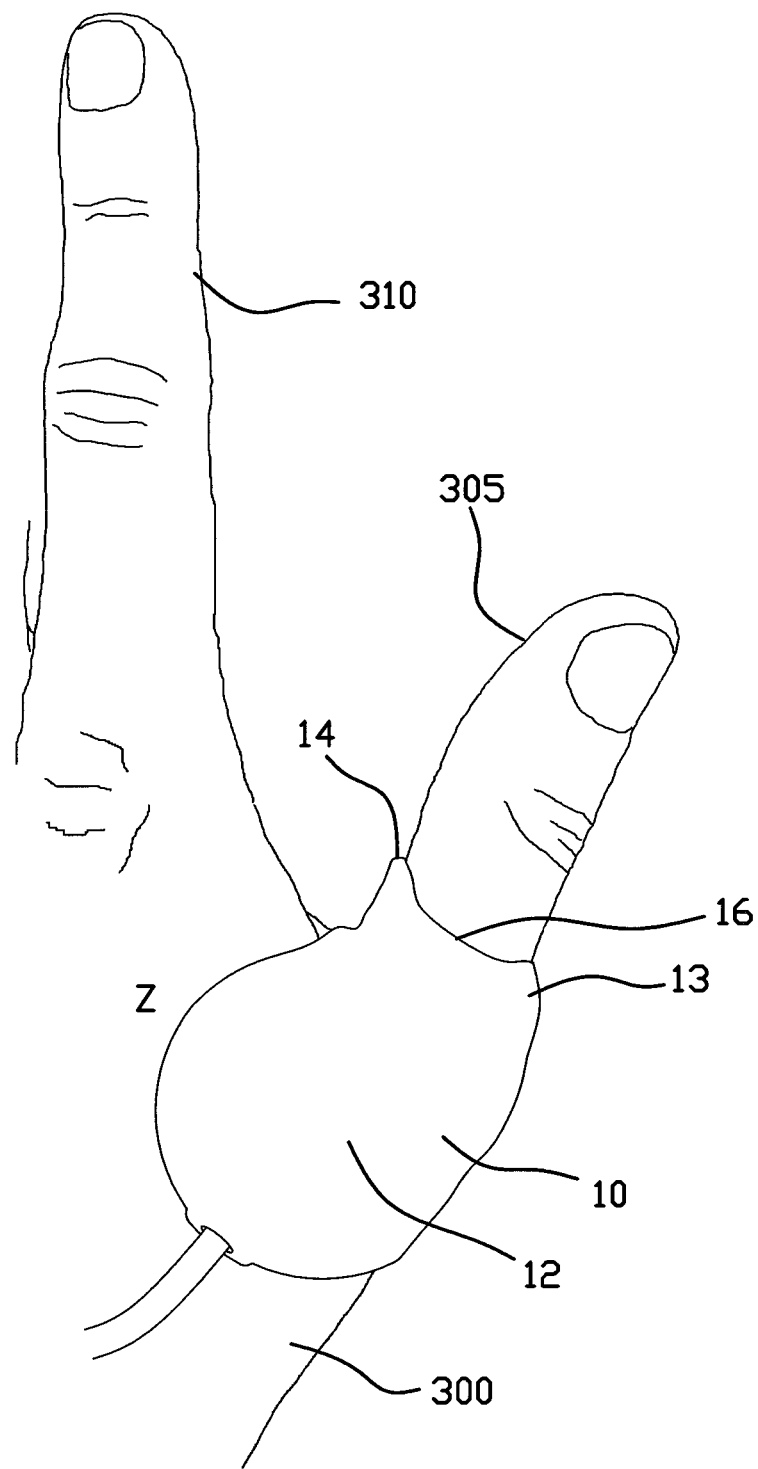

Referring now to FIGS. 3A-C, thereshown is a patient interface as used in the process of FIGS. 4A-B. In FIG. 3A, the patient interface 15 is shown in a first position X such that concave region 16 would lie proximal to the thumb by some amount. Note that wings 13 and 14 are not permanently set around the thumb at this point. A significant portion of the base 12 would cover the thenar eminence 315. A THI measurement would be made at this location. Then, the patient interface may be moved, for example, to the location indicated as Y in FIG. 3B. Here, not only is the concave region 16 over the thumb, so is a portion of the base 12. Little of the base 12 is covering the thenar eminence 315. Another THI measurement would be made here. Then, if the THI measurement at location Y is more desirable the THI measurement at location X, the value at position Y would be stored or otherwise noted (or if this was deemed to be a final test location, the patient interface 10 could be fixed at this location). In our case, we wish to try one more location.

As shown in FIG. 3C, a location Z between locations X and Y is then selected. Here, if a desired THI value is found (we will assume it is) it replaces the previous THI value and if this is the final location to be tested (we will again assume that it is) the patient interface may then be removably affixed to the patient by, for example, removal of the liner (not shown in this figure) and placement of the adhesive onto the tissue. Note that wings 13 and 14 are wrapped partly around the thumb. In a particularly preferred embodiment, the wings are not long enough to wrap entirely around the thumb.

Figure 5A:
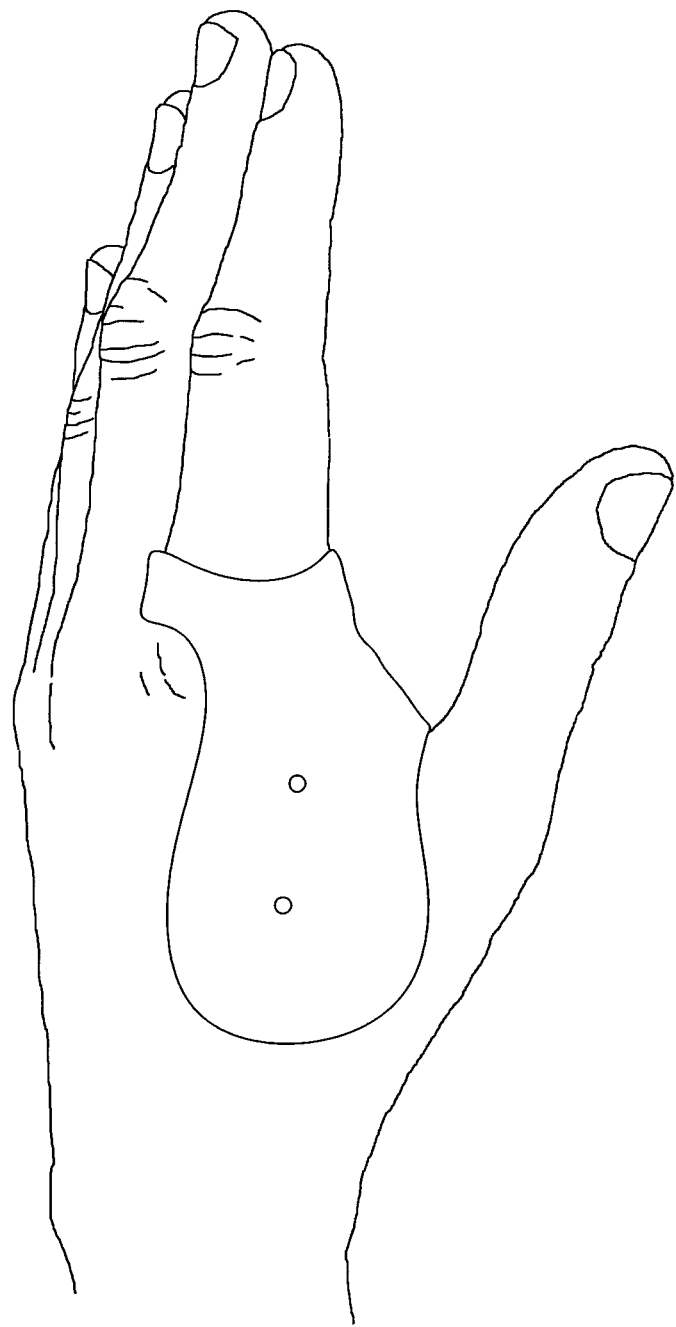
FIGS. 5A-D are perspective views of an alternative placement of the patient interface of FIGS. 2A-B.
Figure 5B:
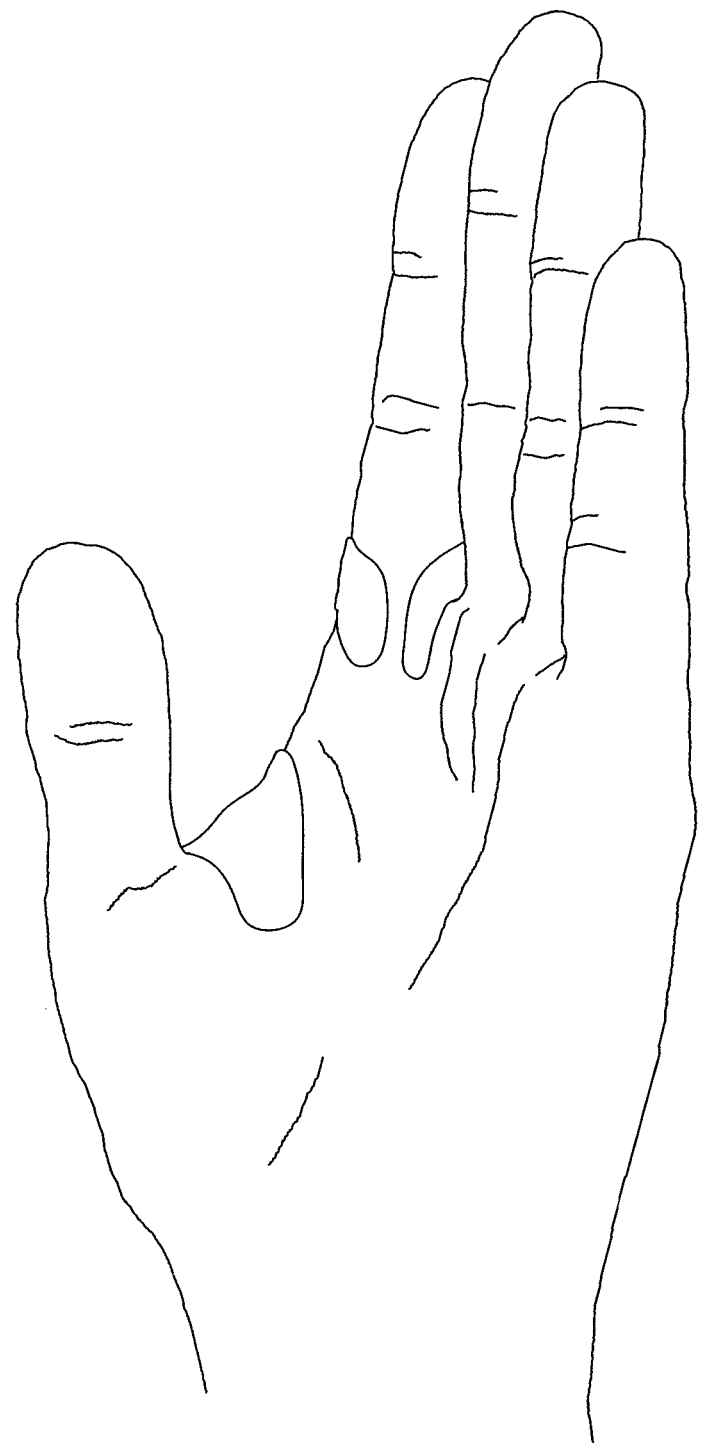
Figure 5C:
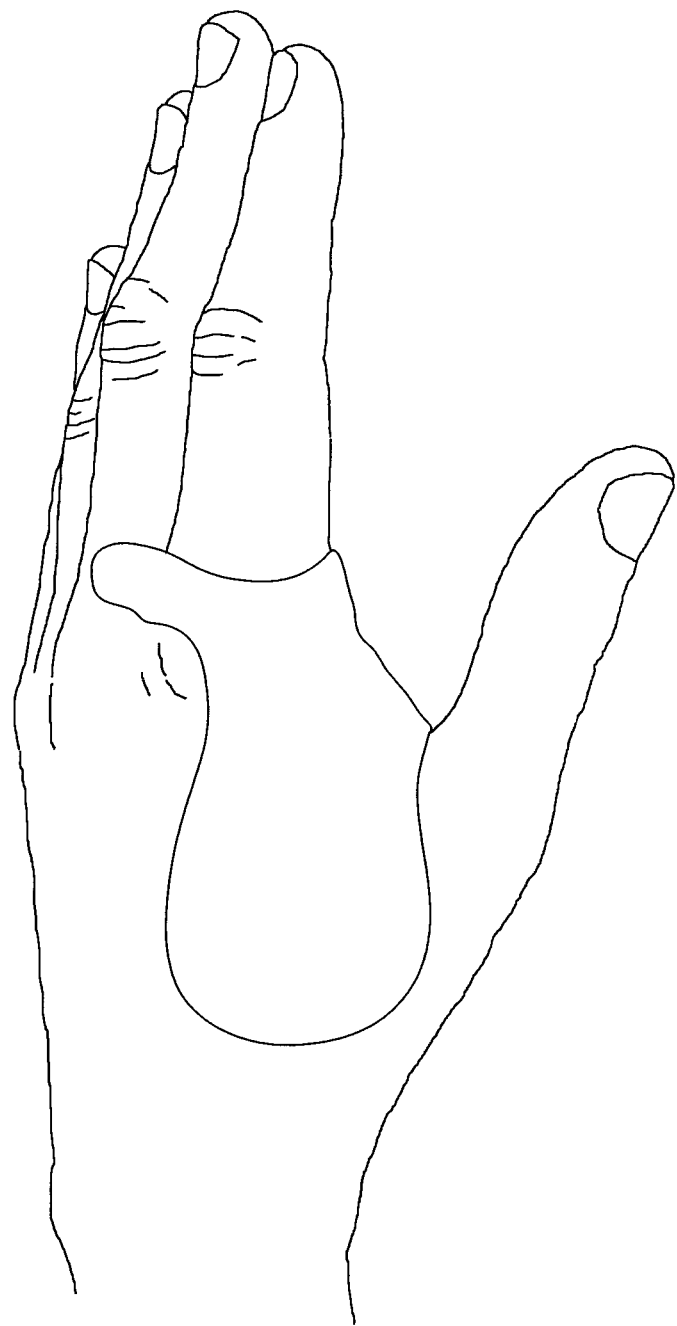
Figure 5D:
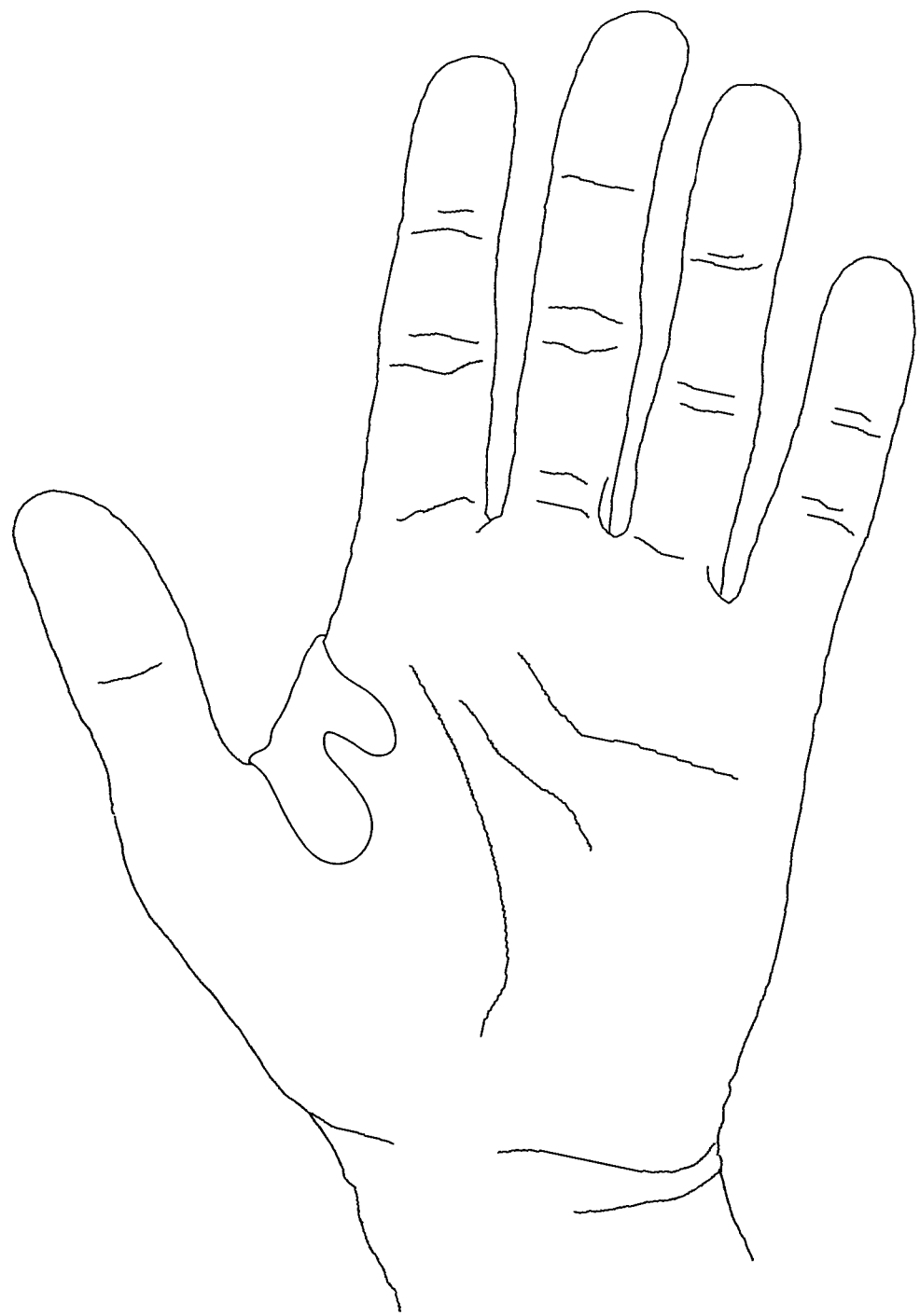

Referring now to FIGS. 5A-D thereshown are alternate locations for the patient interface shown in FIGS. 2A-B. The process followed to place the patient interface here may parallel the process specified in FIGS. 4A-B. In FIGS. 5A-B, the measurement site selected is the first dorsal interosseous. The concave region 16 is located at a side of the index finger distal to the junction of the finger with the hand. The first wing 13 and additional wing 13A are wrapped around between the index finger and thumb on the back side of the hand while the second wing 14 is wrapped around between the index finger and the middle finger on the back side of the hand (see particularly FIG. 5B). The second wing is particularly useful in maintaining a stable attachment to the hand in this location. In FIG. 5C, the concave region 16 is located at the junction of the finger with the hand. Wings 13 and 13A extend between the index finger and the thumb onto the palm as shown in FIG. 5D. Wing 14 may preferably extend in the direction of the middle finger, or wrap around between the index and middle finger.

Figure 7A:
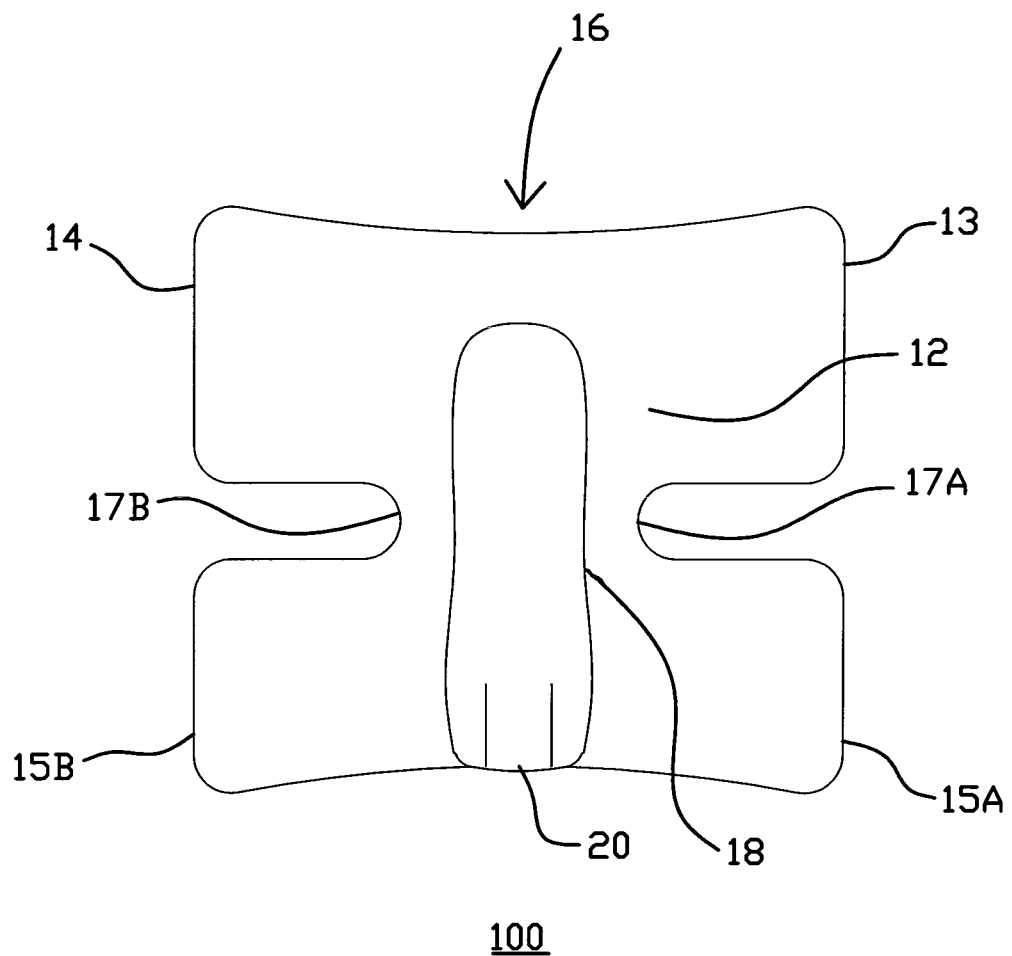
FIGS. 7A-B are top and bottom views of yet another embodiment of the patient interface.
Figure 7B:
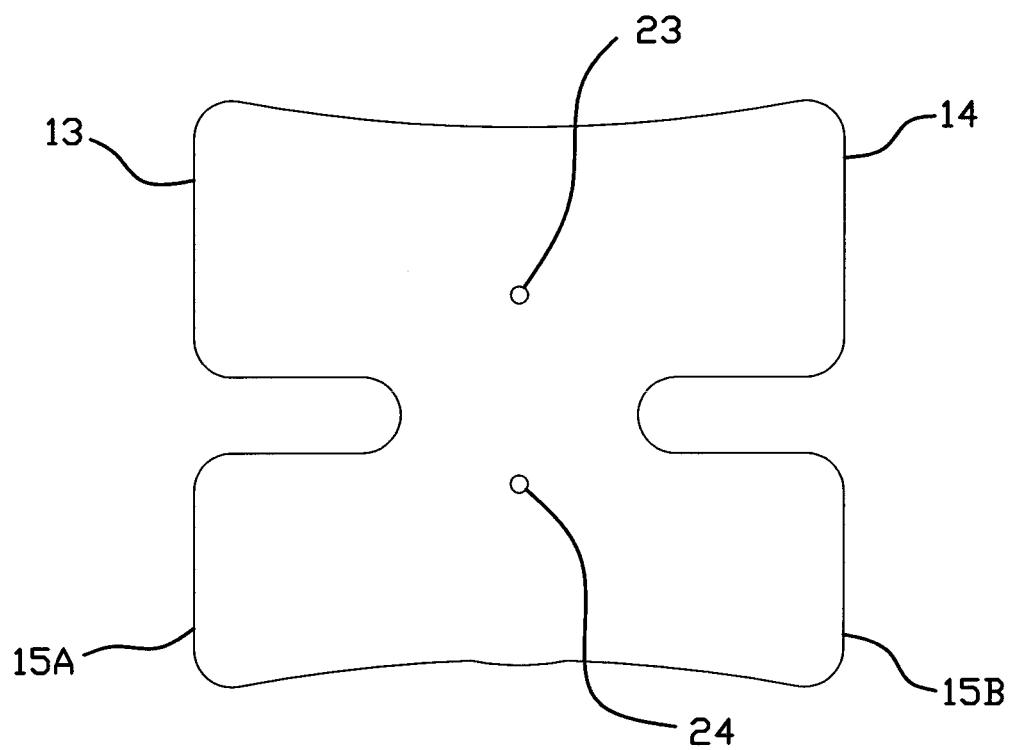

Referring now to FIGS. 7A-B, thereshown are top and bottom views of yet another embodiment of the patient interface of the present invention. The patient interface 100 includes base 12, wings 13 and 14, convex regions 15A and B, concave region 16, pocket 18 and opening 20. Here, unlike the patient interface of FIG. 1, the base 12 does not have a semi-circular portion between convex regions 15A and 15B. Instead, the convex regions are formed similar to the wings 13 and 14. The convex regions 15A and B lead into concave regions 17A and B. By having the separate convex regions and wings, this embodiment of the patient interface is well adapted to mounting on a location where the diameter of the body part on which the patient interface may change from one end of the patient interface to the other. In particular, this interface may be used for measurement of an adult deltoid muscle. Wings 13 and 14 are well adapted to partially wrap around the arm. Concave region 16 serves as a locating feature such as at the junction of the arm with the shoulder. Other locating features such as v shapes or notches are also contemplated.

Figure 6A:
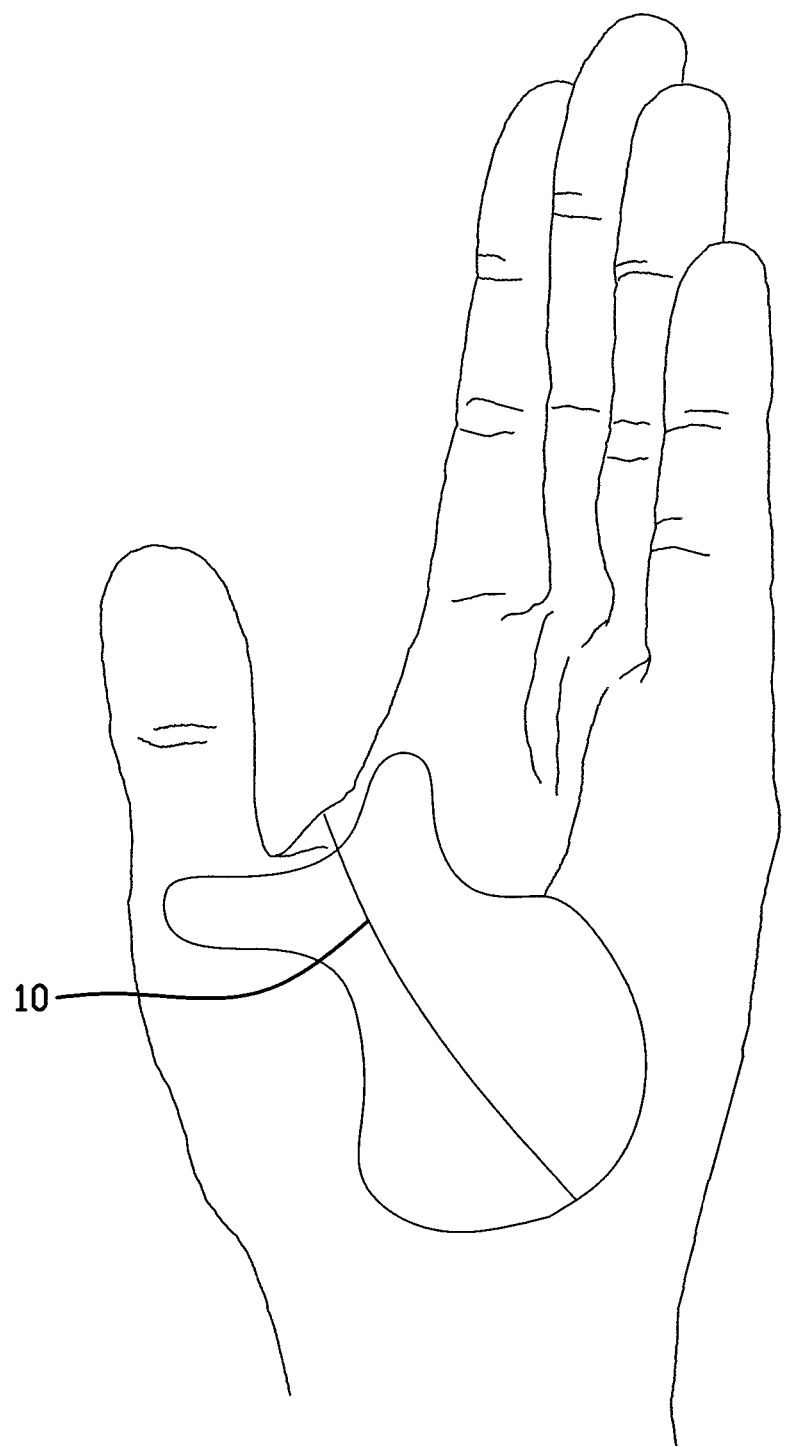
FIGS. 6A-B show an alternate placement of a patient interface proximal to the adductor pollicis.
Figure 6B:
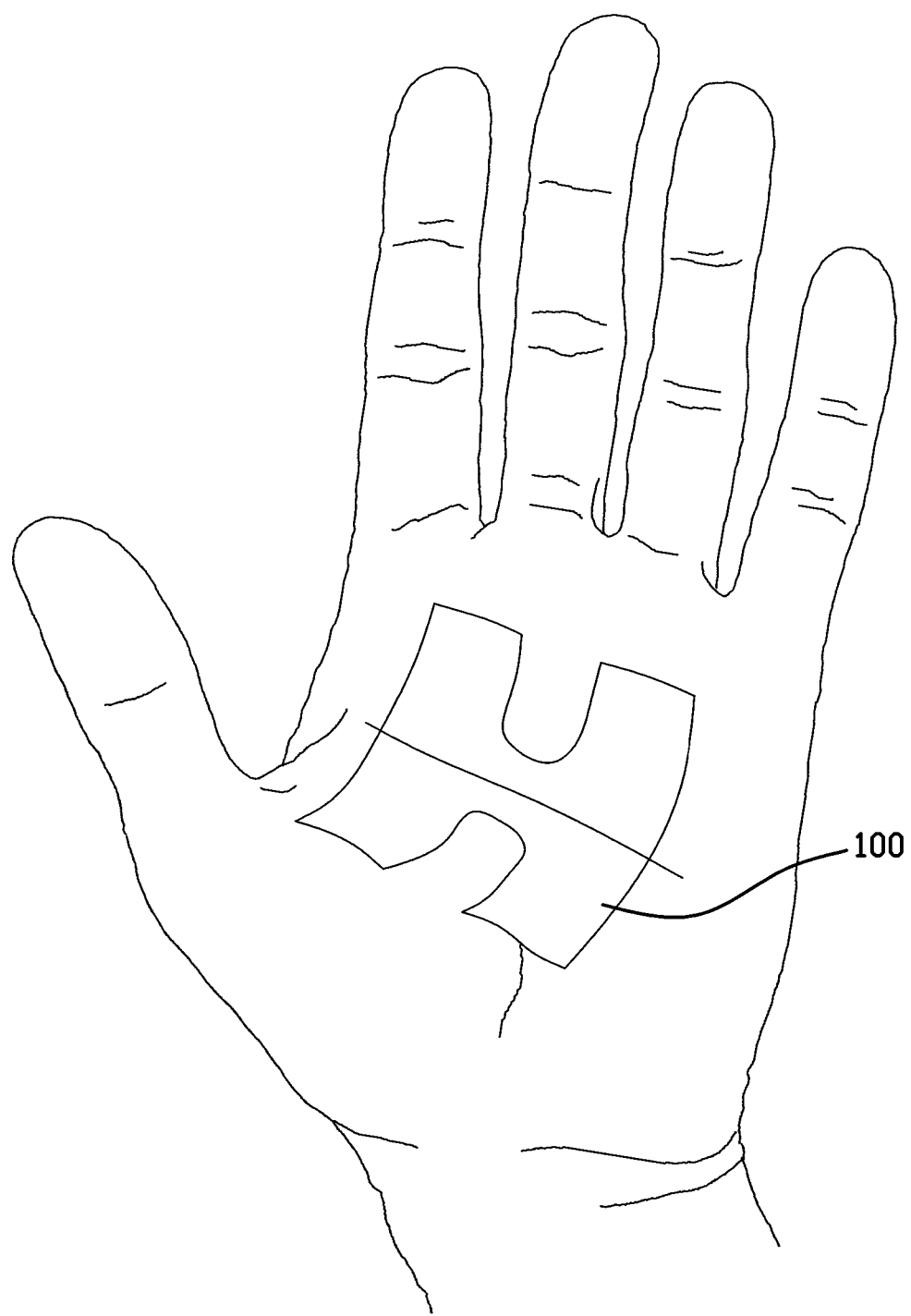

FIG. 6A shows yet another placement of the patient interface of FIG. 1. Here, the patient interface is placed along an axis under which the adductor pollicis muscle runs. The patient interface 10 is placed in a location such that one wing contacts the junction of the thumb with the hand while the other wing contacts the junction of the forefinger with the hand. FIG. 6B shows placement of the patient interface of FIGS. 7A-B along the adductor pollicis muscle. For both FIGS. 6A-B, the base of the patient interface is then placed so that the holes 23 and 24 are aligned along the adductor pollicis muscle.

A common theme among all of the placements is a desire to align the holes 23 and 24 along a longitudinal axis of the muscle. This is a primary reason for having the concave region and wings as shown. This alignment produces a significant signal path for the light to transverse through perfused tissue. Each finger has a muscle known as the lumbrical muscles running axially from the heel of the hand to the junction of the finger with the palm. Each such muscle presents an acceptable site along which the patient interface may be placed. The wings may be extended around the side of a finger with the opposite end of the patient interface (particularly where the opening 20 is located) being positioned generally in alignment with the finger around which the wings have been placed.

Figure 8A:
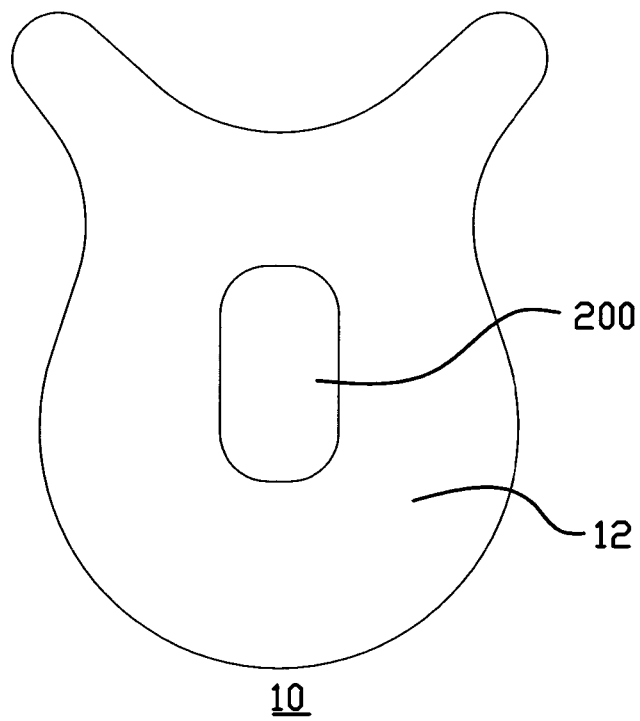
FIGS. 8A-B are top views of two additional interface designs where an optical head may be plugged into the interface.
Figure 8B:
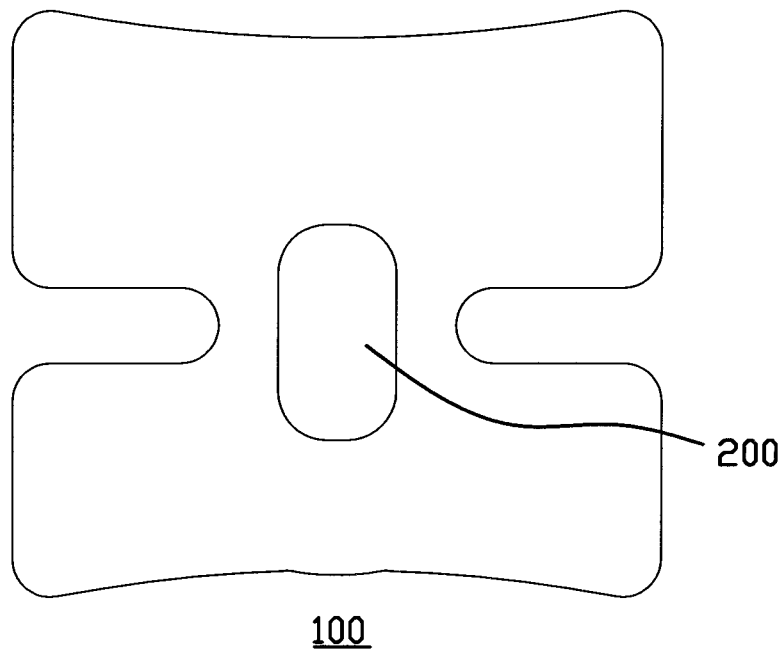

Referring now to FIGS. 8A-B, thereshown are two additional interface designs. In FIG. 8A, an interface 10 similar to the interface of FIG. 1 is shown. Here, however, an optical head may be inserted into opening 200 so that the interface may be left in place at a desired location while allowing for the option of removal of the spectrometer if so desired. An alternative design is shown in FIG. 8B.

Figure 9A:
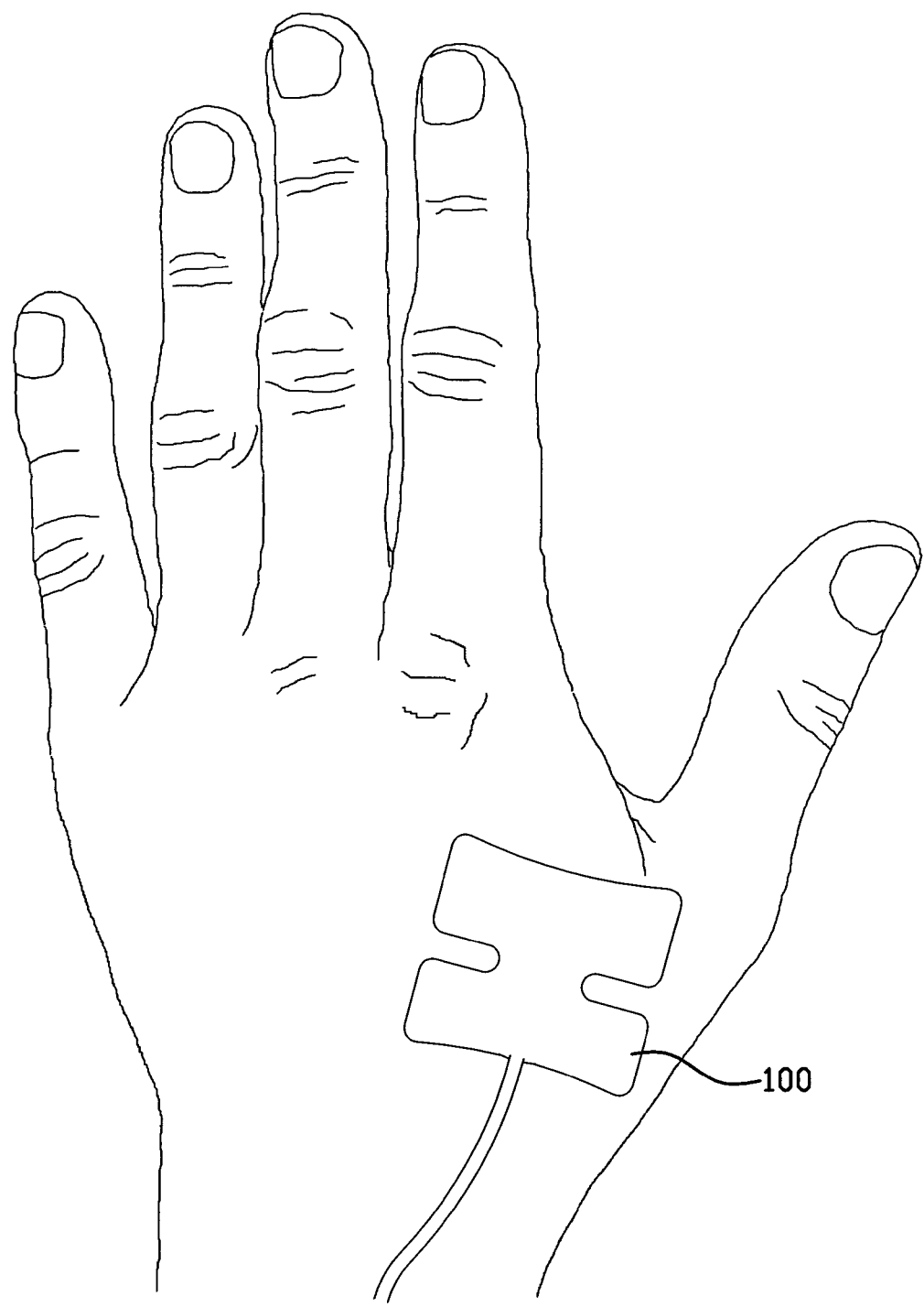
FIGS. 9A-B are a top view of interface locations on the back of the first dorsal interosseous between the finger and thumb and the hypothenar respectively.
Figure 9B:
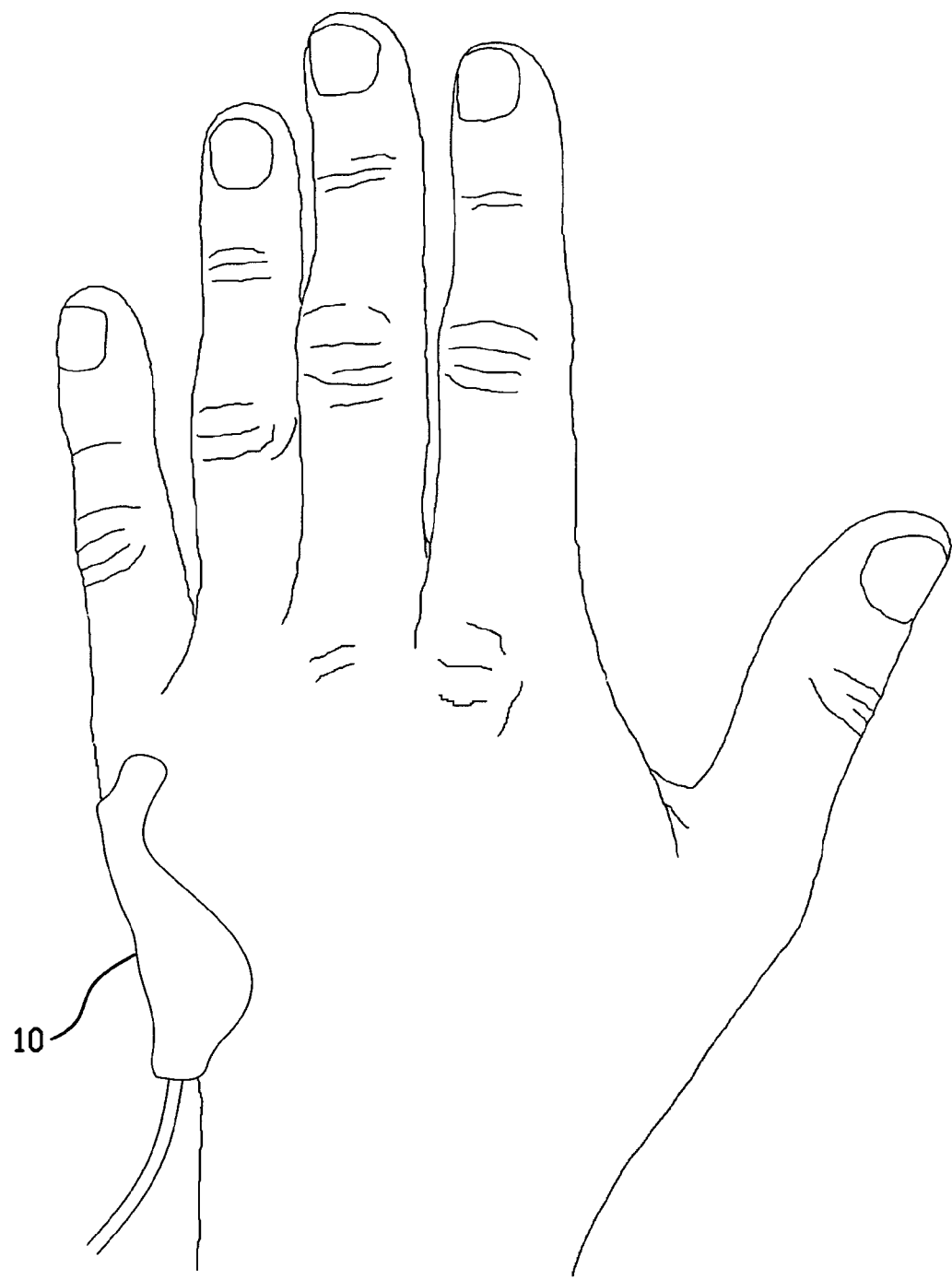

Referring now to FIGS. 9A-B, thereshown are other alternative locations for an interface on a hand. Two preferred locations include the back of the hand on the webspace between the thumb and forefinger (the first dorsal interoseous) (FIG. 9A) and on the hypothenar muscle (FIG. 9B).

Figure 11A:
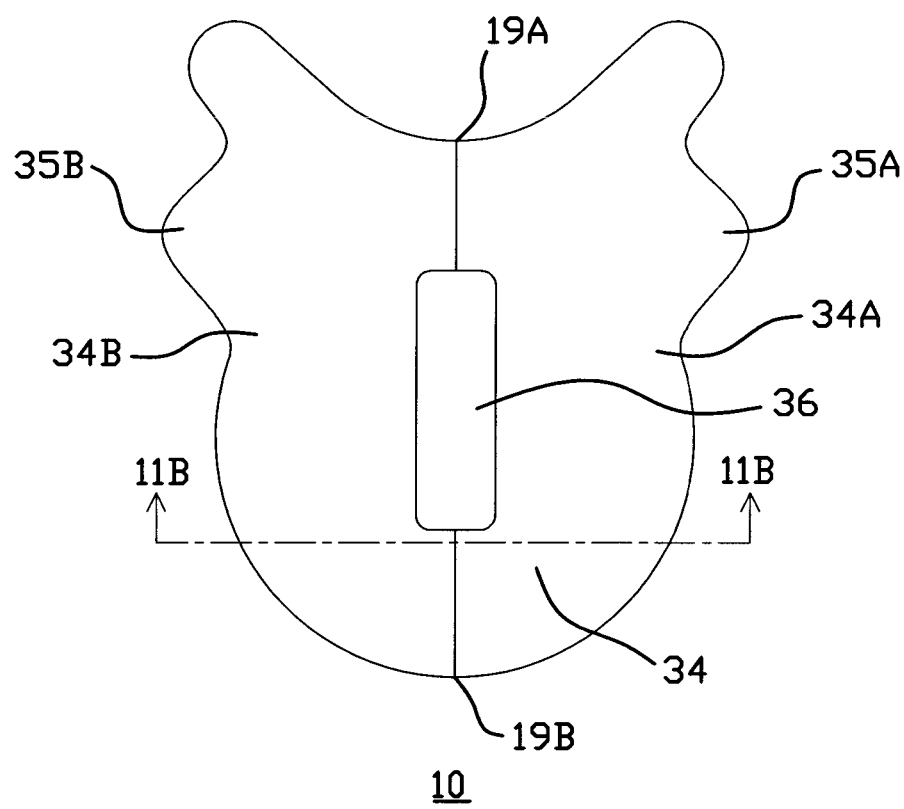
FIG. 11A is a bottom perspective view of a patient interface with an alternative liner.
Figure 11B:
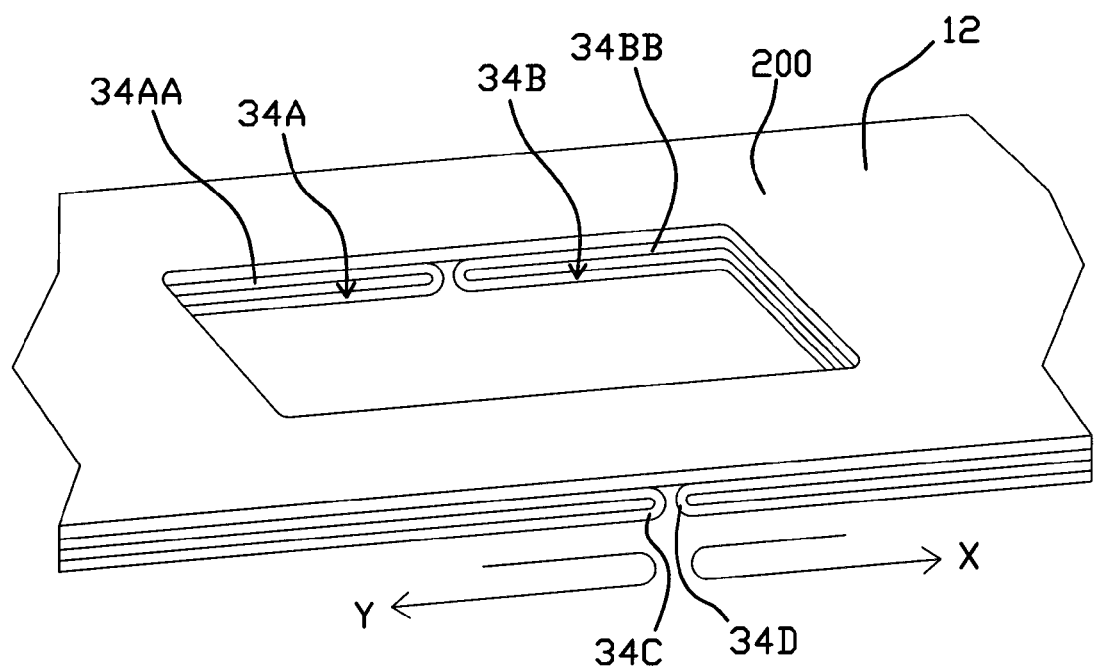
FIG. 11B is a top expanded slice view along line 11B-11B.

In FIGS. 11A and B, thereshown is a "butterfly" version of the liner on the patient interface 10. The base 12 of the patient interface may be formed with a central opening 200 therein. An adhesive (not shown) may be placed on a patient facing portion of the patient interface to facilitate mounting the patient interface on the patient. Split liner 34 may be placed on the adhesive to prevent the patient interface from attaching to anything other than the patient. As can be seen more particularly in FIG. 11B, the split liner may be a folded or hinged, at 34C and D, piece of material that includes a patient side 34A and B and an adhesive side 34AA and BB. To use an interface having the butterfly version of the liner, the interface is lightly placed on the patient at a desired location. While holding the interface in place, tabs 35A and B are then pulled, in a direction normal to axis 19A-B and substantially coplanar with the plane in which sides 34A and B reside. The liner 34 will then move as indicated by arrows X and Y such that adhesive on the interface is then exposed and placed in contact with the patient as the liner is removed.

All publications, patent applications and patents identified in this description are incorporated by reference as if they were fully set out herein

The invention claimed is:

1. A method of locating a patient interface for a tissue measurement instrument on a patient, the patient interface defining a measurement side with one or more holes formed therein through which the tissue measurement instrument is configured to transmit and receive light to measure hemoglobin concentration of tissue, the patient interface having adhesive disposed on the measurement side, the method comprising the steps of:

moving the patient interface around on the tissue in a particular region of the body while measuring hemoglobin concentration until a desired threshold attribute reading of hemoglobin concentration is achieved on the tissue measurement instrument; and upon finding a location where the desired threshold attribute reading is achieved, affixing the patient interface to the patient at the location by adhering the adhesive on the measurement side to the patient.

2. The method of claim 1, wherein:

a liner covers the adhesive on the measurement side; and affixing the patient interface to the patient comprises holding the measurement side of the patient interface against the patient as the liner is removed from the measurement side of the patient interface to expose the adhesive.

3. The method of claim 1, wherein the step of finding the desired threshold attribute reading includes finding a location with at least a two percent tissue hematocrit value.

4. The method of claim 1, further including the step of generally aligning the one or more holes along one of an adductor pollicus, a thenar eminence, a hypo thenar eminence, a digit, a first dorsal interosseous or a deltoid muscle.

5. The method of claim 1, wherein the patient interface has a base defining the measurement side and the one or more holes, the adhesive having at least first and second adhesive regions, the patient interface further having first and second portions covering the first and second adhesive regions respectively, the first portion having a first adhesive facing region attached to the adhesive, a first hinge region and a first patient facing region connected to the first adhesive facing region through the first hinge region, the second portion having a second adhesive facing region attached to the adhesive, a second hinge region and a second patient facing region connected to the second adhesive facing region through the second hinge region, the first and second portions meeting to form a separation, the method further including the steps of:

pulling on the first patient facing region in a direction substantially normal to the separation;

pulling on the second patient facing region in a direction substantially normal to the separation.

6. The method of claim 5, wherein the first patient facing region has a first tab extending beyond the base and the second patient facing region has a second tab extending beyond the base, wherein the step of pulling on the first patient facing region includes pulling on the first tab and the step of pulling on the second patient facing region includes pulling on the second tab.

7. The method of claim 1, wherein the measurement side define both a light transmission hole and a light receipt hole.

8. A method of locating a patient interface for a tissue measurement instrument on a patient, the patient interface having a measurement side with one or more holes formed therein, the measurement side having an adhesive thereon comprising first and second amounts of adhesive, the patient interface further having first and second liners covering the first and second amounts of adhesive respectively, the first liner having a first adhesive facing region attached to the first amount of adhesive, a first hinge region, and a first patient facing region connected to the first adhesive facing region through the first hinge region, the second liner having a second adhesive facing region attached to the second amount of adhesive, a second hinge region, and a second patient facing region connected to the second adhesive facing region through the second hinge region, the first and the second liners forming a separation therebetween, the method comprising the steps of:

moving the patient interface around on the tissue in a particular region of the body until a location where a desired threshold attribute reading is achieved on the tissue measurement instrument is found;

upon finding the location where a desired threshold attribute reading is achieved, firmly holding the patient interface to the patient at the location such that the first patient facing region and the second patient facing region contact the patient;

pulling on the first patient facing region in a direction substantially normal to the separation to remove the first liner from the patient interface while holding the patient interface in place at the location so that the first amount of adhesive on the measurement side of the patient interface is exposed for attachment to the patient;

holding the first amount of exposed adhesive against the patient;

pulling on the second patient facing region in a direction substantially normal to the separation to remove the second liner from the patient interface so that the second amount of adhesive is exposed for attachment to the patient; and holding the second amount of exposed adhesive against the patient.

9. The method of claim 8, wherein:

the tissue measurement instrument is configured to transmit and receive light through the one or more holes on the measurement side to measure hemoglobin concentration of tissue; and the desired threshold attribute reading comprises a measure of hemoglobin concentration of the tissue.

10. The method of claim 8, wherein the step of finding the desired threshold attribute reading includes finding a location with at least a two percent tissue hematocrit value.

11. The method of claim 8, further including the step of generally aligning the one or more holes along one of an adductor pollicus, a thenar eminence, a hypo thenar eminence, a digit, a first dorsal interosseous or a deltoid muscle.

12. The method of claim 8, wherein:

the measurement side defines a light transmission hole and a light receipt hole; and firmly holding the patient interface to the patient at the location comprises holding the patient interface such that the light transmission hole and the light receipt hole align with the longitudinal axis of a muscle from which the desired threshold attribute reading was achieved.

13. The method of claim 8, wherein the first patient facing region has a first tab extending beyond the base and the second patient facing region has a second tab extending beyond the base, wherein the step of pulling on the first patient facing region includes pulling on the first tab and the step of pulling on the second patient facing region includes pulling on the second tab.

14. The method of claim 8, wherein the measurement side defines both a light transmission hole and a light receipt hole.

15. A method of locating a patient interface for a tissue measurement instrument on a patient, the patient interface having a measurement side with one or more holes formed therein, the tissue measurement instrument configured to measure hemoglobin concentration of tissue, the patient interface having adhesive disposed on the measurement side, the method comprising the steps of:
- moving the patient interface around on the tissue along the adductor pollicis muscle while measuring hemoglobin concentration of the adductor pollicis muscle and determining a local maximum of hemoglobin concentration; and
- upon finding the location along the adductor pollicis muscle with the local maximum of hemoglobin concentration, affixing the patient interface to the patient at the location by adhering the adhesive on the measurement side to the patient.

16. The method of claim 15, the method comprising the steps of:
- upon finding the location with the local maximum of hemoglobin concentration, firmly holding the patient interface to the patient at the location;
- partially removing the patient interface from the patient while holding it in place so that a first amount of adhesive on the measurement side of the patient interface may be readied for attachment to the patient;
- placing the first amount of exposed adhesive on the patient;
- partially removing the patient interface in a second direction so that a second amount of adhesive may be readied for attachment to the patient; and
- placing the second amount of exposed adhesive on the patient.

17. The method of claim 15, wherein:
a liner covers the adhesive on the measurement side; and
affixing the patient interface to the patient comprises holding the measurement side of the patient interface against the patient as the liner is removed from the measurement side of the patient interface to expose the adhesive.

18. The method of claim 15, wherein:
the measurement side defines a light transmission hole and a light receipt hole; and
affixing the patient interface to the patient at the location comprises adhering the patient interface such that the light transmission hole and the light receipt hole align with the longitudinal axis of the adductor pollicis muscle.

19. The method of claim 15, wherein the patient interface has a base defining the measurement side and the one or more holes, the adhesive having at least first and second adhesive regions, the patient interface further having first and second portions covering the first and second adhesive regions respectively, the first portion having a first adhesive facing region attached to the adhesive, a first hinge region, and a first patient facing region connected to the first adhesive facing region through the first hinge region, the second portion having a second adhesive facing region attached to the adhesive, a second hinge region, and a second patient facing region connected to the second adhesive facing region through the second hinge region, the first and second portions meeting to form a separation, the method further including the steps of:
- pulling on the first patient facing region in a direction substantially normal to the separation;
- pulling on the second patient facing region in a direction substantially normal to the separation.

20. The method of claim 19, wherein the first patient facing region has a first tab extending beyond the base and the second patient facing region has a second tab extending beyond the base, wherein the step of pulling on the first patient facing region includes pulling on the first tab and the step of pulling on the second patient facing region includes pulling on the second tab.

21. The method of claim 15, wherein the measurement side defines both a light transmission hole and a light receipt hole.

* * * * *